(12) United States Patent
Meadows et al.

(10) Patent No.: US 7,177,691 B2
(45) Date of Patent: Feb. 13, 2007

(54) IMPLANTABLE PULSE GENERATORS USING RECHARGEABLE ZERO-VOLT TECHNOLOGY LITHIUM-ION BATTERIES

(75) Inventors: Paul M Meadows, Glendale, CA (US); Carla Mann Woods, Los Angeles, CA (US); Hisashi Tsukamoto, Saugus, CA (US); Joey Chen, Arcadia, CA (US)

(73) Assignee: Advanced Bionics Corporation, Valencia, CA (US)

( * ) Notice: Subject to any disclaimer, the term of this patent is extended or adjusted under 35 U.S.C. 154(b) by 527 days.

(21) Appl. No.: 10/419,002

(22) Filed: Apr. 18, 2003

(65) Prior Publication Data

US 2003/0191504 A1    Oct. 9, 2003

Related U.S. Application Data

(62) Division of application No. 09/627,803, filed on Jul. 28, 2000, now Pat. No. 6,553,263.

(60) Provisional application No. 60/146,571, filed on Jul. 30, 1999.

(51) Int. Cl.
*A61N 1/375* (2006.01)
(52) U.S. Cl. ............................ 607/36; 607/46; 607/43; 607/61; 607/33
(58) Field of Classification Search .................. 607/33, 607/46, 61, 36, 43
See application file for complete search history.

(56) References Cited

U.S. PATENT DOCUMENTS 3,454,012 A     7/1969   Raddi (Continued)

FOREIGN PATENT DOCUMENTS

JP          01006384 A2      1/1989

(Continued)

OTHER PUBLICATIONS

Broussely, et al., "Lithium Insertion Into Host Materials: the Key to Success for Li Ion Batteries", Electrochimica Acta, vol. 45, (1999) pp. 3-22.

(Continued)

*Primary Examiner*—Jeffrey R. Jastrzab
(74) *Attorney, Agent, or Firm*—Bryant R. Gold; Victoria A. Poissant

(57) ABSTRACT

An implantable medical device, such as an implantable pulse generator (IPG) used with a spinal cord stimulation (SCS) system, includes a rechargeable lithiumion battery having an anode electrode with a substrate made substantially from titanium. Such battery construction allows the rechargeable battery to be discharged down to zero volts without damage to the battery. The implantable medical device includes battery charging and protection circuitry that controls the charging of the battery so as to assure its reliable and safe operation. A multi-rate charge algorithm is employed that minimizes charging time while ensuring the battery cell is safely charged. Fast charging occurs at safer lower battery voltages (e.g., battery voltage above about 2.5 V), and slower charging occurs when the battery nears full charge higher battery voltages (e.g., above about 4.0 V). When potentially less-than-safe very low voltages are encountered (e.g., less than 2.5 V), then very slow (trickle) charging occurs to bring the battery voltage back up to the safer voltage levels where more rapid charging can safely occur. The battery charging and protection circuitry also continuously monitors the battery voltage and current. If the battery operates outside of a predetermined range of voltage or current, the battery protection circuitry disconnects the battery from the particular fault, i.e. charging circuitry or load circuits.

5 Claims, 12 Drawing Sheets

U.S. PATENT DOCUMENTS

| | | | |
|---|---|---|---|
| 3,646,940 A | 3/1972 | Timm et al. | |
| 3,724,467 A | 4/1973 | Avery et al. | |
| 3,822,708 A | 7/1974 | Zilber | |
| 3,824,129 A | 7/1974 | Fagan, Jr. | |
| 3,867,950 A | 2/1975 | Fischell | |
| 3,888,260 A | 6/1975 | Fischell | |
| 3,942,535 A | 3/1976 | Schulman | |
| 4,014,346 A | 3/1977 | Brownlee et al. | |
| 4,082,097 A | 4/1978 | Mann et al. | |
| 4,092,464 A | 5/1978 | Dey et al. | |
| 4,231,027 A | 10/1980 | Mann et al. | |
| 4,338,945 A | 7/1982 | Kosugi et al. | |
| 4,345,603 A | 8/1982 | Schulman | |
| 4,379,462 A | 4/1983 | Borkan et al. | |
| 4,431,001 A | 2/1984 | Hakansson et al. | |
| 4,935,316 A | 6/1990 | Redey | |
| 5,053,297 A | 10/1991 | Yamahira et al. | |
| 5,065,083 A | 11/1991 | Owens | |
| 5,121,754 A | 6/1992 | Mullett | |
| 5,264,201 A | 11/1993 | Dahn et al. | |
| 5,278,000 A | 1/1994 | Huang et al. | |
| 5,391,193 A | 2/1995 | Thompson | |
| 5,411,537 A | 5/1995 | Munshi et al. | |
| 5,417,719 A | 5/1995 | Hull et al. | |
| 5,478,674 A | 12/1995 | Miyasaka | |
| 5,500,583 A | 3/1996 | Buckley et al. | |
| 5,501,703 A | 3/1996 | Holsheimer et al. | |
| 5,545,191 A | 8/1996 | Mann et al. | |
| 5,578,398 A | 11/1996 | Jenkins et al. | |
| 5,591,546 A | 1/1997 | Nagaura | |
| 5,614,331 A | 3/1997 | Takeuchi et al. | |
| 5,631,100 A | 5/1997 | Yoshino et al. | |
| 5,690,693 A | 11/1997 | Wang et al. | |
| 5,702,431 A * | 12/1997 | Wang et al. | 607/61 |
| 5,733,313 A * | 3/1998 | Barreras et al. | 607/33 |
| 5,749,909 A | 5/1998 | Schroeppel et al. | |
| 5,783,333 A | 7/1998 | Mayer | |
| 5,828,202 A | 10/1998 | Tamai | |
| 5,948,006 A | 9/1999 | Mann | |
| 6,017,654 A | 1/2000 | Kumta et al. | |
| 6,067,474 A | 5/2000 | Schulman et al. | |
| 6,124,062 A | 9/2000 | Horie et al. | |
| 6,159,636 A | 12/2000 | Wang et al. | |
| 6,181,105 B1 | 1/2001 | Cutolo et al. | |
| 6,181,969 B1 | 1/2001 | Gord | |
| 6,185,452 B1 | 2/2001 | Schulman et al. | |
| 6,185,454 B1 | 2/2001 | Thompson | |
| 6,198,969 B1 | 3/2001 | Kuzma | |
| 6,204,634 B1 | 3/2001 | Zimmerman et al. | |
| 6,207,326 B1 | 3/2001 | Kawakami et al. | |
| 6,208,894 B1 | 3/2001 | Schulman et al. | |
| 6,245,464 B1 | 6/2001 | Spillman et al. | |
| 6,249,703 B1 | 6/2001 | Stanton et al. | |
| 6,263,245 B1 | 7/2001 | Snell | |
| 6,275,737 B1 | 8/2001 | Mann | |
| 6,516,227 B1 | 2/2003 | Meadows et al. | |
| 6,596,439 B1 | 7/2003 | Tsukamoto et al. | |
| 6,677,080 B2 | 1/2004 | Tanizaki et al. | |
| 7,101,642 B2 | 9/2006 | Tsukamoto et al. | |
| 2002/0076612 A1 | 6/2002 | Tanizaki et al. | |
| 2002/0086216 A1 | 7/2002 | Sekino et al. | |
| 2003/0143465 A1 | 7/2003 | Takahashi et al. | |

FOREIGN PATENT DOCUMENTS

| | | |
|---|---|---|
| JP | 01014881 A2 | 1/1989 |
| JP | 64002258 A2 | 1/1989 |
| JP | 02-174070 | 7/1990 |
| JP | 03-192663 | 8/1991 |
| JP | 05047369 A2 | 2/1993 |
| JP | 05047384 A2 | 2/1993 |
| JP | 05-074462 | 3/1993 |
| JP | 05-151995 | 6/1993 |
| JP | 05-174872 | 7/1993 |
| JP | 05-325968 | 10/1993 |
| JP | 06203829 A1 | 7/1994 |
| JP | 06-349493 | 12/1994 |
| JP | 07335263 A1 | 12/1995 |
| JP | 08-022841 | 1/1996 |
| JP | 08185851 A1 | 7/1996 |
| JP | 08222272 A1 | 8/1996 |
| JP | 11288704 A1 | 10/1999 |
| JP | 200260475 A2 | 9/2000 |
| WO | WO 99/50925 A1 | 10/1999 |
| WO | WO 01/82398 A1 | 11/2001 |
| WO | WO03/005465 A1 | 1/2003 |
| WO | WO 03/044880 A1 | 5/2003 |

OTHER PUBLICATIONS

Colbow, et al., "Structure and Electrochemistry of the Spinel Ozides $LiTi_2O_4$ and $Li_{4/3}Ti_{5/3}O_4$", Journal of Power Sources, vol. 26 (1989), pp. 397-402.

Dan, et al., "More Details on the New $LiMnO_2$ Rechargeable Battery Technology Developed at Tadiran", Journal of Power Sources, vol. 68, (1997), pp. 443-447.

Lee, et al., "Synthesis and Electrochemical Characterization of Orthorhombic $LiMnO_2$ Material", Department of Applied Chemistry, Saga University, Honjo 1, Saga 840-8505, Japan (1 page).

Linden, et al., Handbook of Batteries, 2nd Ed., Copyright 1995 by McGraw-Hill, Inc., New York, pp. 36.4-36.17.

Tsukamoto, et al., "Synthesis and Electrochemical Studies of Lithium Transition Metal Oxides for Lithium-ion Batteries", Department of Chemistry, University of Aberdeen, 1999.

* cited by examiner

IMPLANTABLE PULSE GENERATORS USING RECHARGEABLE ZERO-VOLT TECHNOLOGY LITHIUM-ION BATTERIES

This application is a divisional of U.S. application Ser. No. 09/627,803, filed Jul. 28, 2000 now U.S. Pat. No. 6,553,263, which claims the benefit of U.S. Provisional Application Ser. No. 60/146,571, filed Jul. 30, 1999, which provisional application is incorporated herein by reference.

BACKGROUND OF THE INVENTION

The present invention relates generally to implantable pulse generators, e.g., a pulse generator used within a Spinal Cord Stimulation (SCS) system or other type of neural stimulation system. More particularly, the present invention relates to the use of a rechargeable zero-volt technology lithium-ion battery within such an implantable pulse generator.

Implantable pulse generators (IPG) are devices that generate electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a spinal cord stimulation system. A spinal cord stimulation system is a programmable implantable pulse generating system used to treat chronic pain by providing electrical stimulation pulses from an electrode array placed epidurally near a patient's spine. SCS systems consist of several components, including implantable and external components, surgical tools, and software. The present invention provides an overview an SCS system and emphasizes the use of a rechargeable zero volt technology battery within such a system, including the charging system used for charging the rechargeable battery.

Spinal cord stimulation is a well-accepted clinical method for reducing pain in certain populations of patients. SCS systems typically include an implantable pulse generator, lead wires, and electrodes connected to the lead wires. The pulse generator delivers electrical pulses to the dorsal column fibers within the spinal cord through the electrodes implanted along the dura of the spinal cord. The attached lead wires exit the spinal cord and are tunneled around the torso of the patient to a subcutaneous pocket where the pulse generator is implanted.

Spinal cord and other stimulation systems are known in the art, however, to applicants' knowledge, none teach the use of a rechargeable zero-volt technology battery within the implanted portion of the system, with accompanying charging and protection circuitry, as proposed herein. For example, in U.S. Pat. No. 3,646,940, there is disclosed an implantable electronic stimulator that provides timed sequenced electrical impulses to a plurality of electrodes so that only one electrode has a voltage applied to it at any given time. Thus, the electrical stimuli provided by the apparatus taught in the '940 patent comprise sequential, or non-overlapping, stimuli.

In U.S. Pat. No. 3,724,467, an electrode implant is disclosed for the neural stimulation of the spinal cord. A relatively thin and flexible strip of physiologically inert plastic is provided with a plurality of electrodes formed thereon. The electrodes are connected by leads to a RF receiver, which is also implanted and controlled by an external controller. The implanted RF receiver has no power storage means, and must be coupled to the external controller in order for neural stimulation to occur.

In U.S. Pat. No. 3,822,708, another type of electrical spinal cord stimulating device is shown. The device has five aligned electrodes that are positioned longitudinally on the spinal cord and transversely to the nerves entering the spinal cord. Current pulses applied to the electrodes are said to block sensed intractable pain, while allowing passage of other sensations. The stimulation pulses applied to the electrodes are approximately 250 microseconds in width with a repetition rate of from 5 to 200 pulses per second. A patient-operable switch allows the patient to change which electrodes are activated, i.e., which electrodes receive the current stimulus, so that the area between the activated electrodes on the spinal cord can be adjusted, as required, to better block the pain. Other representative patents that show spinal cord stimulation systems or electrodes include U.S. Pat. Nos. 4,338,945; 4,379,462; 5,121,754; 5,417,719 and 5,501,703.

The dominant SCS products that are presently commercially available attempt to respond to three basic requirements for such systems: (1) providing multiple stimulation electrodes to address variable stimulation parameter requirements and multiple sites of electrical stimulation signal delivery; (2) allowing modest to high stimulation currents for those patients who need it; and (3) incorporating an internal power source with sufficient energy storage capacity to provide several years of reliable service to the patient. Unfortunately, not all of these features are available in any one device. For example, one known device has a limited battery life at only modest current outputs, and has only a single voltage source, and hence only a single stimulation channel (programmable voltage regulated output source), which provides a single fixed pattern to up to four electrode contacts. Another known device offers higher currents that can be delivered to the patient, but does not have a battery, and thus requires the patient to wear an external power source and controller. Even then, such device still has only one voltage source, and hence only a single stimulation channel, for delivery of the current stimulus to multiple electrodes through a multiplexer. Yet a third known device provides multiple channels of modest current capability, but does not have an internal power source, and thus also forces the patient to wear an external power source and controller. It is thus seen that each of the systems, or components, disclosed or described above suffers from one or more shortcomings, e.g., no internal power storage capability, a short operating life, none or limited programming features, large physical size, the need to always wear an external power source and controller, the need to use difficult or unwieldy surgical techniques and/or tools, unreliable connections, and the like. What is clearly needed, therefore, is a spinal cord stimulation system that is superior to existing systems by providing longer life through the use of a rechargeable battery, easier programming and more stimulating features in a smaller package without compromising reliability.

Regardless of the application, all implantable pulse generators are active devices requiring energy for operation, either powered by an implanted battery or an external power source. It is desirable for the implantable pulse generator to operate for extended periods of time with little intervention by the patient or caregiver. However, devices powered by primary (non-rechargeable) batteries have a finite lifetime before the device must be surgically removed and replaced. Frequent surgical replacement is not an acceptable alternative for many patients. If a battery is used as the energy source, it must have a large enough storage capacity to operate the device for a reasonable length of time. For low-power devices (less than 100 μW) such as cardiac pacemakers, a primary battery may operate for a reasonable length of time, often up to ten years. However, in many neural stimulation applications such as SCS, the power requirements are considerably greater due to higher stimulation rates, pulse widths, or stimulation thresholds. Powering these devices with conventional primary batteries would require considerably larger capacity batteries to operate them for a reasonable length of time, resulting in devices so large that they may be difficult to implant or, at the very least, reduce patient comfort. Therefore, in order to maintain a device size that is conducive to implantation, improved primary batteries with significantly higher energy densities are needed. However, given the state of the art in battery technology, the required energy density is not achievable at the present time.

If an implanted battery is not used as the power source, then a method is required to transcutaneously supply power to the IPG on a continuous basis. For applications that require large amounts of power such as heart pumps and other heart-assist devices, an external power source is the preferred choice. Power can be supplied to the device via a percutaneous cable, or more preferably and less invasively, coupled to the device through electromagnetic induction. The external power source can be an AC outlet or a DC battery pack, which may be recharged or replaced with new batteries when depleted. However, these systems obviously require the patient to continually wear an external device to power the implanted pulse generator, which may be unacceptable for many patients because they are often bulky and uncomfortable to wear, and naturally, limit patient mobility.

One alternative power source is the secondary, or rechargeable battery, where the energy in these batteries can be replenished by recharging the batteries on a periodic basis. It is known in the art to use a rechargeable battery within an implant device. See, e.g., U.S. Pat. No. 4,082,097, entitled "Multimode Recharging System for Living Tissue Stimulators", and applicant Carla Mann Wood's U.S. patent application Ser. No. 09/048,826, filed Mar. 25, 1998, entitled "System of Implantable Devices For Monitoring and/or Affecting Body Parameters", now U.S. Pat. No. 6,208,894 which patent and patent application are likewise incorporated herein by reference. The devices and methods taught in this patent and application, however, comprise specialized devices, e.g., microstimulators, or relate to specific applications, e.g., cardiac pacing, which impose unique requirements not applicable to many IPG applications. Cardiac pacemakers with rechargeable batteries have been developed in the past; see U.S. Pat. Nos. 3,454,012; 3,824,129; 3,867,950; 3,888,260; and 4,014,346. However, these devices were met with limited success in regards to battery performance and market acceptance. Many of these devices were powered by nickel-cadmium (NiCd) batteries. NiCd's low volumetric energy density of 100 Wh/liter provided limited energy storage, and frequent charging was required. Also, its low nominal cell voltage of 1.2 V required many cells to be stacked in series, requiring cells to be closely matched for optimum performance. NiCd batteries also suffered from a phenomenon called "memory effect," which causes the cell to lose capacity if cycled at shallow discharge depths. Moreover, NiCd batteries have a high self-discharge rate, losing approximately 30% of their capacity per month at body temperatures. Also, cycle life performance was poor, as NiCd batteries typically lasted fewer than 300 cycles. In addition, charging NiCd batteries was often problematic because the standard charge termination method for NiCd batteries is somewhat complicated, requiring the need to detect a zero or negative voltage slope (dV/dt) and/or temperature slope (dT/dt). When NiCd batteries are overcharged, an exothermic reaction occurs: oxygen gas given off at the nickel electrode recombines with the cadmium electrode to form cadmium hydroxide. Cell leakage or venting can occur as a result of the pressure increase in the cell. Furthermore, there may be disposal issues with NiCd batteries, as cadmium is highly toxic to the environment.

Newer battery technologies have been developed in recent years. The Nickel Metal-Hydride (NiMH) battery was developed to improve upon NiCd performance. NiMH batteries were first commercially introduced in 1990, and are in many ways similar to NiCd batteries. The main exception is the replacement of the cadmium electrode with a metal-hydride alloy, resulting in more than twice the volumetric energy density (>200 Wh/liter). In addition, the metal-hydride is less toxic than cadmium. However, NiMH batteries suffer from some of the same drawbacks as well, including low cell voltage (1.2 V), high self-discharge (>30% per month), difficult charge termination, low cycle life (<300 cycles), and to a lesser extent, memory effect.

Rechargeable lithium-based batteries were first developed in the 1970s using lithium metal as the active electrode material. Lithium has great promise as a battery material because it is the lightest of all metals, with high cell voltage (>3 V) and high energy density. However, lithium metal in its pure form is extremely reactive, and proved to be very unstable as a battery electrode as employed in early designs. In 1990, however, Sony Corporation introduced a safer rechargeable lithium-based battery called lithium-ion (Li-ion), which used a lithium composite oxide ($LiCoO_2$) cathode and a lithium-intercalating graphite anode. Lithium ions, or $Li^+$, instead of lithium metal, are shuttled back and forth between the electrodes (hence the nick-name, "rocking-chair" battery). Lithium-ion is superior to other rechargeable battery chemistries, with the highest volumetric energy density (>300 Wh/liter) and gravimetric energy density (>100 Wh/kg). In addition, Lithium-ion batteries have a high nominal voltage of 3.6 V, as well as low self-discharge (less than 10% per month), long cycle life (>500), and no memory effect. Charge termination for Lithium-ion batteries is also simpler than that of NiCd and NiMH batteries, requiring only a constant voltage cutoff. However, Lithium-ion batteries are not as tolerant to overcharging and overdischarging. If significantly overcharged, Lithium-ion batteries may go into "thermal runaway," a state in which the voltage is sufficiently high to cause the electrode/electrolyte interface to breakdown and evolve gas, leading to self-sustaining exothermic reactions. As a result, cell leakage or venting can occur. If Lithium-ion batteries are over-discharged (<1 V), the negative electrode may dissolve and cause plating of the electrodes. This can lead to internal shorts within the cell, as well as possible thermal runaway. Therefore, careful monitoring of the cell voltage is paramount, and battery protection circuitry is necessary to keep the cell in a safe operating region.

It is known in the art to use a Lithium-ion battery in an implantable medical device, see. e.g., U.S. Pat. Nos. 5,411, 537 and 5,690,693. However, such disclosed use requires careful avoidance of overcharge and overdischarging conditions, as outlined above, else the implant battery, and hence the implant device, is rendered useless.

The most recent development in rechargeable battery technology is the Lithium-ion polymer battery. Lithium-ion polymer batteries promise higher energy density, lower self-discharge and longer cycle life compared to conventional aqueous electrolyte Lithium-ion batteries. Its chemical composition is nearly identical to that of conventional Lithium-ion batteries with the exception of a polymerized electrolyte in place of the aqueous electrolyte. The polymer electrolyte enables the battery to be made lighter and thinner than conventional Lithium-ion batteries by utilizing foil packaging instead of a metal can, thus allowing it to be conformable to many form factors. Lithium-ion polymer batteries are also theoretically safer since the polymer electrolyte behaves more benignly when overcharged, generating less heat and lower internal cell pressure. Unfortunately, commercial realization of Lithium-ion polymer batteries has been slow and fraught with early production problems. Only recently have the major battery manufacturers (Sony, Panasonic, Sanyo) announced plans for Lithiumion polymer battery production.

What is clearly needed for neural stimulation applications is a physically-small power source that either provides a large energy reservoir so that the device may operate over a sufficiently length of time, or a replenishable power source that still provides sufficient energy storage capacity to allow operation of the device over relatively long period of time, and which then provides a convenient, easy and safe way to refill the energy reservoir, i.e., recharge the battery, so that the device may again operate over a relatively long period of time before another refilling of the reservoir (recharging of the battery) is required.

SUMMARY OF THE INVENTION

A spinal cord stimulation (SCS) system that uses a rechargeable battery has been invented that is superior to existing systems. Because physically-small power sources suitable for implantation having sufficient capacity to power most neural stimulation applications do not yet exist, the power source used in an neural stimulation IPG (or other implantable medical device application) in accordance with the teachings of the present invention is a rechargeable battery. More particularly, the present invention is directed to the use of a rechargeable lithium-ion or lithium-ion polymer battery within an implantable medical device, such as an implantable pulse generator (IPG), coupled with the use of appropriate battery protection and battery charging circuits.

In accordance with one aspect of the invention, therefore, a lithium-ion or lithium-ion polymer rechargeable battery is used in combination with appropriate battery protection and charging circuitry housed within an implantable medical device, e.g., an IPG, of a medical system, e.g., an SCS system. Such use of a rechargeable battery advantageously assures the safe and reliable operation of the system over a long period of time. While a preferred embodiment of the invention is represented and described herein by way of a spinal cord stimulation (SCS) system, it is to be emphasized that the invention—directed to the use of a lithium-ion or lithium-ion polymer rechargeable battery in an implanted medical device, including appropriate battery protection and battery charging circuitry—may be used within any implantable medical device.

The representative SCS system with which the lithium-ion based rechargeable battery is employed in accordance with the present invention provides multiple channels, each able to produce up to 20 mA of current into a 1 Ω load. To provide adequate operating power for such a system, the SCS system employs a rechargeable battery and charging/protection system that allows the patient to operate the device independent of external power sources or controllers. Moreover, the implanted battery is rechargeable using non-invasive means, meaning that the battery can be recharged as needed when depleted by the patient with minimal inconvenience. Advantageously, the SCS system herein described requires only an occasional recharge, is smaller than existing implant systems, has a life of at least 10 years at typical settings, offers a simple connection scheme for detachably connecting a lead system thereto, and is extremely reliable.

A key element of the SCS system herein described (or other system employing an implantable pulse generator, or "IPG") is the use of a rechargeable lithiumion or lithium-ion polymer battery. Lithium-ion batteries offer several distinct advantages over other battery chemistries: high volumetric and gravimetric energy densities, high cell voltage, long cycle life, simple detection of charge termination, low toxicity, and no memory effect.

The lithium-ion or lithium-ion polymer battery used in the SCS system described herein is specifically designed for implantable medical devices. It incorporates several distinct features compared to conventional lithium-ion batteries. The battery case is made from a high-resistivity Titanium alloy to reduce heating from eddy currents induced from the electromagnetic field produced by inductive charging. The case is also hermetically-sealed to increase cycle life and shelf life performance. Most importantly, the battery is specifically designed to allow discharge to zero volts without suffering irreversible damage, which feature is referred to herein as "zero-volt technology". This feature is significant because conventional lithium-ion batteries can not operate at low voltages (less than about 1 V) without damage occurring to the negative electrode. Thus, should an implant device with a conventional lithium-ion battery be operated until the implanted battery is nearly discharged (~2.5 V), and if the battery is not subsequently recharged for any one of many reasons, the battery will naturally self-discharge to below 1 V in less than six months. If this occurs, the performance and safety of the cell may be compromised. In contrast, the present invention relates to an implantable electrical stimulator capable of recharging its lithiumion battery from an electrical potential of 0 V up to normal operating voltages, e.g., approximately 4 V. The invention takes advantage of new battery technology that allows discharge down to 0 V without damage to the cell.

In accordance with one aspect of the present invention, the SCS system utilizes a non-invasive, electromagnetic induction system to couple the energy from an external power source to the implanted charging circuitry for recharging the battery. The charging circuitry contains a charge controller that converts the unregulated induced power into the proper charging current. The level of the charging current is determined by a state machine-type algorithm that monitors the voltage level of the battery. In one embodiment, when the battery voltage is below 1 V, for example, the battery is charged with a very low current of C/50 (1/50 of the battery capacity) or less. When the battery voltage surpasses 1 V, the battery is charged at a rate of approximately C/25. When the battery voltage surpasses 2.5 V, the battery is charged at the maximum charge rate of approximately C/2, until the battery voltage nears its desired full-charge voltage, at which point the charge rate may again be reduced. That is, fast charging occurs at the safer lower battery voltages (e.g., voltage above about 2.5 V), and slower charging occurs when the battery nears full charge higher battery voltages (above about 4.0 V). When potentially less-than-safe very low voltages are encountered (e.g., less than 2.5 V), then very slow (trickle) charging occurs to bring the battery voltage back up to the safer voltage levels where more rapid charging can safely occur. This multi-rate charge algorithm minimizes charging time while ensuring the cell is safely charged. The charging circuitry also contains a battery protection circuit that continuously monitors the battery voltage and current. If the battery operates outside of a predetermined range of voltage or current, the battery protection circuitry disconnects the battery from the particular fault, i.e. charging circuitry or load circuits. Moreover, the charging circuitry is able to monitor the state-of-charge of the battery by measuring the voltage of the battery, since there is good correlation between battery voltage and state of charge in lithium-ion batteries.

In accordance with another aspect of the invention, an external charging system is provided that supplies the energy to the rechargeable battery of the IPG device. Such external charging system may take one of several forms or embodiments. In one embodiment, the external charger is powered by an alternating current (AC) power supply and is manually controlled by the patient. In another embodiment, the external charger is powered by an AC power supply and is automatically controlled by the external controller for the implanted device. Such embodiment necessarily employs a suitable communication link between the external controller and the external charger, the communication link comprising, e.g., a cable (hard wire connection), an infrared (IR) link, or a radio frequency (RF) link. In another preferred embodiment, the external charger is itself powered by a battery, which battery may be a replaceable (primary) battery, or a rechargeable battery.

The external charger may thus assume one of several forms, ranging from a table-top AC powered device to a small portable (mobile) device that uses a primary or secondary battery to transfer energy to the implanted device. In all instances, the electrical circuitry within the implanted device has final control upon the acceptance or rejection of incoming energy. The external charging system, however, is optimally controlled so that its operation is terminated if the implanted device does not require the external energy.

In operation, the SCS system (or other system employing an IPG) monitors the state of charge of the internal battery and controls the charging process. Then, through a suitable communication link, the SCS system is able to inform the patient or clinician regarding the status of the system, including the state of charge, and makes requests to initiate an external charge process. In this manner, the acceptance of energy from the external charger is entirely under the control of the implant circuitry, e.g., the IPG, and several layers of physical and software control may be used, as desired or needed, to ensure reliable and safe operation of the charging process. The use of such a rechargeable power source thus greatly extends the useful life of the SCS system, or other IPG systems. This means that once the IPG is implanted, it can, under normal conditions, operate for many years without having to be explanted.

All of the above and other features combine to provide a SCS system employing an IPG or similar implantable electrical stimulator (or other implantable electrical circuitry, such as an implantable sensor) having a rechargeable battery that is markedly improved over what has heretofore been available.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

At the outset, it is noted that the present invention may be used with an implantable pulse generator (IPG), or similar electrical stimulator and/or electrical sensor, that may be used as a component of numerous different types of stimulation systems. The description that follows relates to use of the invention within a spinal cord stimulation (SCS) system. However, it is to be understood that the invention is not so limited. Rather, the invention may be used with any type of implantable electrical circuitry that could benefit from deriving its operating power from a rechargeable battery.

Further, while the invention is described in connection with its use within an SCS system, it is noted that a complete description of the SCS system is not provided herein. Rather, only those portions of the SCS system that relate directly to the present invention are disclosed. A more complete description of the SCS system may be found in U.S. Pat. No. 6,516,227, application Ser. No. 09/626,010, filed Jul. 26, 2000, which application is incorporated herein by reference.

Figure 1:
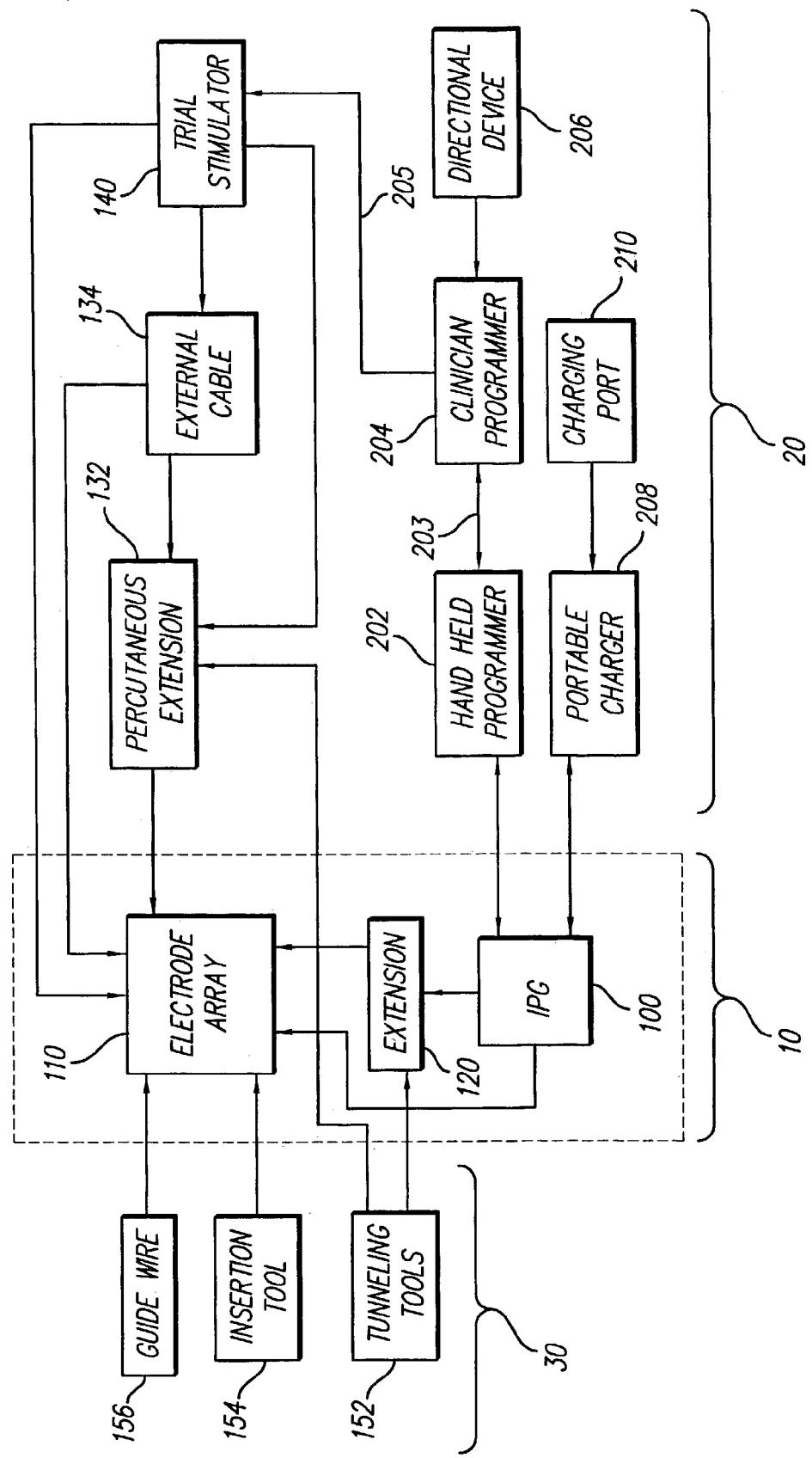
FIG. 1 is a block diagram that illustrates the various implantable, external, and surgical components of an SCS system that employs an implantable pulse generator (IPG) having a rechargeable battery in accordance with the present invention.

Turning first to FIG. 1, a block diagram is shown that illustrates the various components of an SCS system wherein the invention may be used. These components may be subdivided into three broad categories: (1) implantable components 10, (2) external components 20, and (3) surgical components 30. As seen in FIG. 1, the implantable components 10 include an implantable pulse generator (IPG) 100, an electrode array 110, and (as needed) a lead extension 120. The extension 120 is used to electrically connect the electrode array 110 to the IPG 100. In a preferred embodiment, the IPG 100, described more fully below in connection with FIG. 4 or 5, comprises a rechargeable, multichannel, 16 contact, telemetry-controlled, pulse generator housed in a rounded high-resistivity titanium alloy case to reduce eddy current heating during the inductive charging process. The preferred embodiment includes 16 current sources, each with a programmable amplitude such that the device is a current-regulated, rather than a voltage-regulated system. Four pulse timing generators are used to create 4 independent groups in which any of 16 electrodes can be included in a positive or negative polarity. A connector that forms an integral part of the IPG 100 allows the electrode array 110 or extension 120 to be detachably secured, i.e., electrically connected, to the IPG 100. This connector may be of the type described in U.S. patent application Ser. No. 09/239,926, filed Jan. 28, 1999, incorporated herein by reference.

The IPG 100 contains stimulating electrical circuitry ("stimulating electronics"), a power source, e.g., a rechargeable battery, and a telemetry system. Typically, the IPG 100 is placed in a surgically-made pocket either in the abdomen, or just at the top of the buttocks. It may, of course, also be implanted in other locations of the patient's body. Once implanted, the IPG 100 is connected to the lead system, comprising the lead extension 120, if needed, and the electrode array 110. The lead extension 120, for example, may be tunneled up to the spinal column. Once implanted, the lead system 110 and lead extension 120 are intended to be permanent. In contrast, the IPG 100 may be replaced when its power source fails or is no longer rechargeable.

Advantageously, the IPG 100 can provide electrical stimulation through a multiplicity of electrodes, e.g., sixteen electrodes, included within the electrode array 110.

Figure 2:
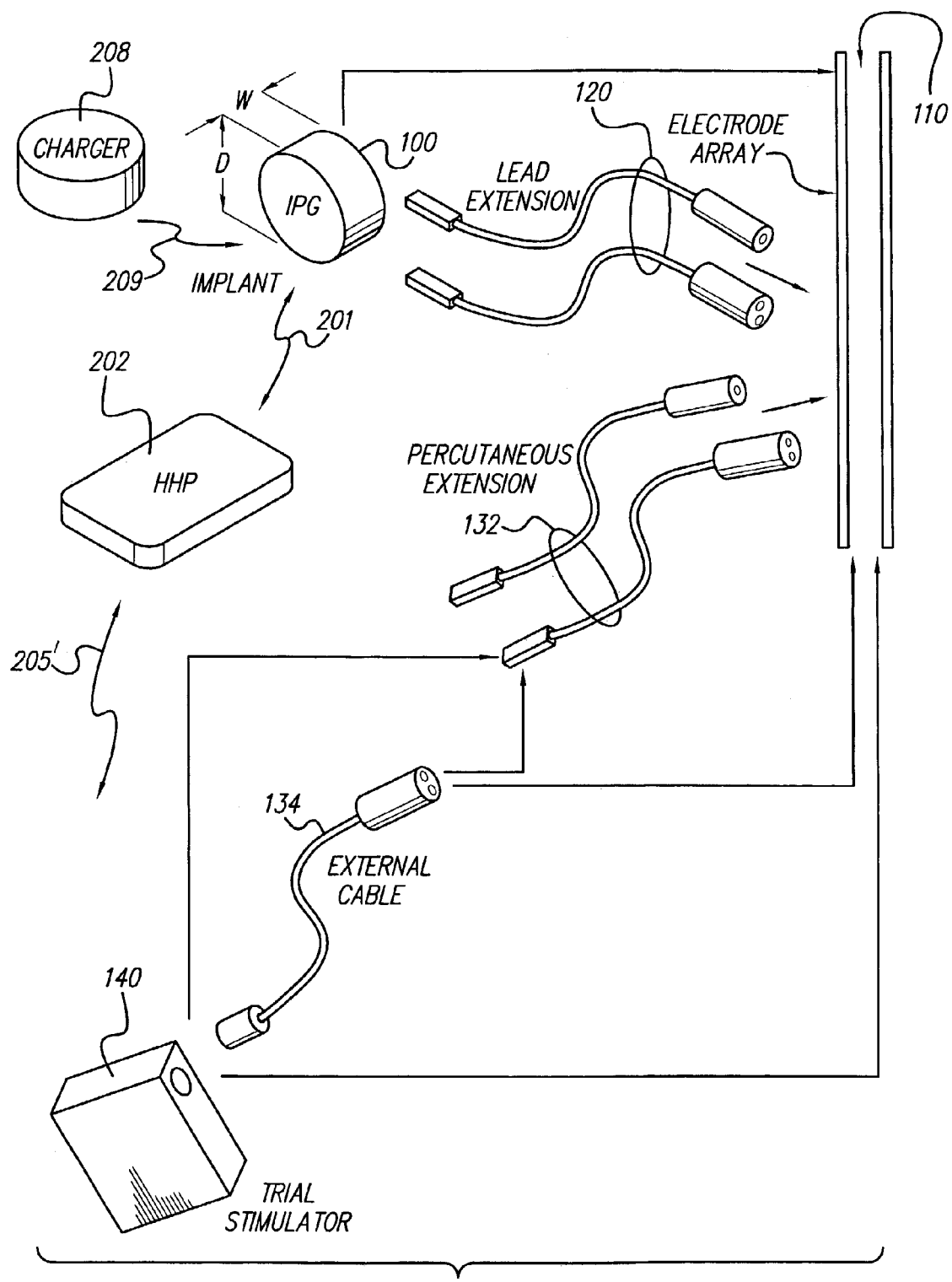
FIG. 2 shows various components of the SCS system of FIG. 1.

As seen best in FIG. 2, and as also illustrated in FIG. 1, the electrode array 110 and its associated lead system typically interface with the implantable pulse generator (IPG) 100 via a lead extension system 120. The electrode array 110 may also be connect to an external trial stimulator 140, through the use of a percutaneous lead extension 132 and/or an external cable 134. The external trail stimulator 140 includes the same pulse generation circuitry as does the IPG 100, and is used on a trial basis for, e.g., 7–10 days after the electrode array has been implanted, prior to implantation of the IPG 100, in order to test the effectiveness of the stimulation that is to be provided.

Still with reference to FIG. 2 and FIG. 1, the hand-held programmer (HHP) 202 may be used to control the IPG 100 via a suitable non-invasive communications link 203, e.g., an RF link. Such control allows the IPG 100 to be turned ON or OFF, and generally allows stimulation parameters, e.g., pulse amplitude, width, and rate, to be set within prescribed limits. The HHP may also be linked with the external trial stimulator 140 through another link 205', e.g., an infra red link. Detailed programming of the IPG 100 is preferably accomplished through the use of an external clinician's programmer 204 (FIG. 1) which is coupled to the IPG 100 through the HHP 202. An external charger 208, non-invasively coupled with the IPG 100 through link 209, e.g., an inductive link, allows energy stored or otherwise made available to the charger 208 to be coupled into the rechargeable battery housed within the IPG 100.

Figure 3:
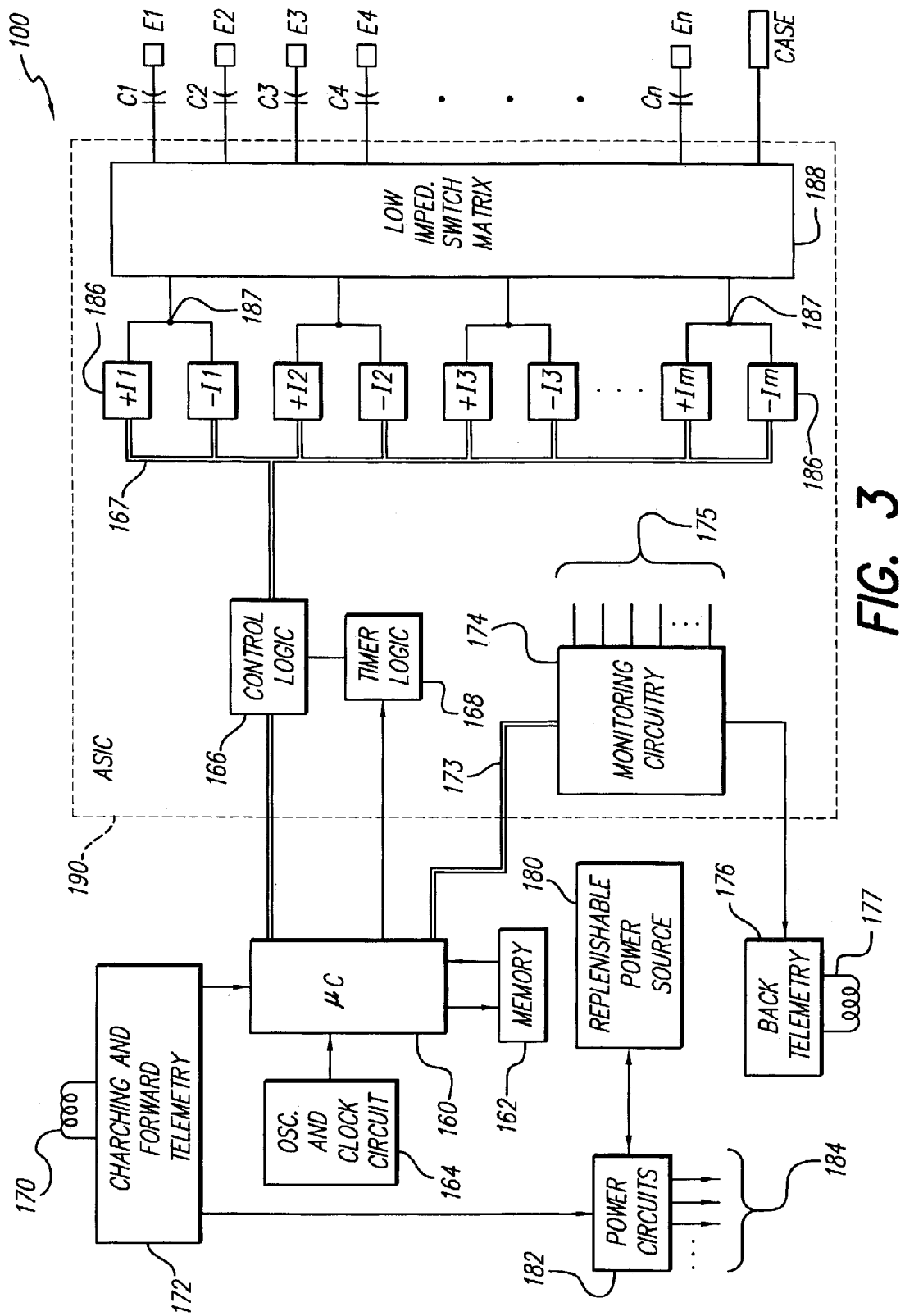
FIG. 3 is a block diagram that illustrates the main components, including a rechargeable battery, of one embodiment of an implantable pulse generator (IPG) used with the invention.

Turning next to FIG. 3, a block diagram is shown that illustrates the main components of one embodiment of an implantable pulse generator (IPG) 100 that may be used with the invention. As seen in FIG. 3, the IPG includes a microcontroller (µC) 160 connected to memory circuitry 162. The µC 160 typically comprises a microprocessor and associated logic circuitry, which in combination with control logic circuits 166, timer logic 168, and an oscillator and clock circuit 164, generate the necessary control and status signals which allow the µC to control the operation of the IPG in accordance with a selected operating program and stimulation parameters. The operating program and stimulation parameters are typically stored within the memory 162 by transmitting an appropriate modulated carrier signal through a receiving coil 170 and charging and forward telemetry circuitry 172 from an external programming unit, e.g., a handheld programmer 202 and/or a clinician programmer 204, assisted as required through the use of a directional device 206 (see FIG. 1). (The handheld programmer is thus considered to be in "telecommunicative" contact with the IPG; and the clinician programmer is likewise considered to be in telecommunicative contact with the handheld programmer, and through the handheld programmer, with the IPG.) The charging and forward telemetry circuitry 172 demodulates the carrier signal it receives through the coil 170 to recover the programming data, e.g, the operating program and/or the stimulation parameters, which programming data is then stored within the memory 162, or within other memory elements (not shown) distributed throughout the IPG 100.

The microcontroller 160 is further coupled to monitoring circuits 174 via bus 173. The monitoring circuits 174 monitor the status of various nodes or other points 175 throughout the IPG 100, e.g., power supply voltages, current values, temperature, the impedance of electrodes attached to the various electrodes E1 . . . En, and the like. Informational data sensed through the monitoring circuit 174 may be sent to a remote location external to the IPG (e.g., a non-implanted location) through back telemetry circuitry 176, including a transmission coil 177.

The operating power for the IPG 100 is derived from a rechargeable power source 180. In accordance with the teachings of the present invention, such rechargeable power source 180 comprises a lithium-ion or lithium-ion polymer battery. The advantages of using such batteries have been previously discussed. The rechargeable battery 180 provides an unregulated voltage to power circuits 182. The power circuits 182, in turn, generate the various voltages 184, some of which are regulated and some of which are not, as needed by the various circuits located within the IPG. A particular feature of the present invention is the manner in which recharging occurs, on an as-needed basis, and wherein the power circuits 182 control the charging operation so that only energy that is needed is allowed to charge the battery, thereby preventing overcharging from occurring.

As indicated previously, the power source 180 of the IPG 100 comprises a rechargeable lithium-ion or lithium-ion polymer battery. Recharging occurs inductively from an external charger (shown below in FIGS. 7 and 9) to an implant depth of approximately 2 to 3 cm. For safety reasons, only authorized charging devices may be used to recharge the battery. The battery is chargeable to 80% of its capacity within two hours. Moreover, at an 80% charge, a single battery discharge is able to support stimulation at typical parameter settings on one channel (electrode group) for at least about three weeks; and on 4 channels for approximately one week, after 10 years of cycling. Additionally, the IPG 100 is able to monitor and telemeter the status of its rechargeable battery 180 each time a communication link is established with the external patient programmer 202. Typically, a telecommunicative link is established, and hence battery monitoring may occur, each time a programming event occurs, i.e., each time the patient or medical personnel change a stimulus parameter.

As described, it is thus seen that any of the n electrodes may be assigned to up to k possible groups (where k is an integer corresponding to the number of channels, and in a preferred embodiment is equal to 4). Moreover, any of the n electrodes can operate, or be included in, any of the k channels. The channel identifies which electrodes are selected to synchronously source or sink current in order to create an electric field. Amplitudes and polarities of electrodes on a channel may vary, e.g., as controlled by the patient hand held programmer 202. External programming software in the clinician programmer 204 is typically used to set parameters including electrode polarity, amplitude, pulse rate and pulse width for the electrodes of a given channel, among other possible programmable features.

Hence, it is seen that each of the n programmable electrode contacts can be programmed to have a positive (sourcing current), negative (sinking current), or off (no current) polarity in any of the k channels. Moreover, it is seen that each of the n electrode contacts can operate in a bipolar mode or multipolar mode, e.g., where two or more electrode contacts are grouped to source/sink current at the same time. Alternatively, each of the n electrode contacts can operate in a monopolar mode where, e.g., the electrode contacts associated with a channel are configured as cathodes (negative), and the case electrode, on the IPG case, is configured as an anode (positive).

Further, in the preferred embodiment, the amplitude of the current pulse being sourced or sunk from a given electrode contact may be programmed to one of several discrete current levels, e.g. ±0 to ±10 mA, in steps of 0.1 mA. Also, in the preferred embodiment, the pulse width of the current pulses is adjustable in convenient increments. For example, the pulse width range is preferably at least 0 to 1 milliseconds (ms) in increments of 10 microseconds (μs). Similarly, in the preferred embodiment, the pulse rate is adjustable within acceptable limits. For example, the pulse rate preferably spans 0–1000 Hz. Other programmable features can include slow start/end ramping, burst stimulation cycling (on for X time, off for Y time), and open or closed loop sensing modes.

The stimulation pulses generated by the IPG 100 are charged balanced. This means that the amount of positive charge associated with a given stimulus pulse must be offset with an equal and opposite negative charge. Charge balance may be achieved through a coupling capacitor, which provides a passive capacitor discharge that achieves the desired charge balanced condition. Alternatively, active biphasic or multi-phasic pulses with positive and negative phases that are balanced may be used to achieve the needed charge balanced condition.

The type of bidirectional current sources depicted in FIG. 3 may be realized by those of skill in the art using the teachings of U.S. Pat. No. 6,181,969, application Ser. No. 09/338,700, filed Jun. 23, 1999, entitled "Programmable Current Output Stimulus Stage for Implantable Device", which patent is incorporated herein by reference.

Advantageously, by using current sources of the type disclosed in the referenced patent application, or equivalent, the IPG 100 is able to individually control the n electrode contacts associated with the n electrode nodes E1, E2, E3, . . . En. Controlling the current sources and switching matrix 188 using the microcontroller 160, in combination with the control logic 166 and timer logic 168, thereby allows each electrode contact to be paired or grouped with other electrode contacts, including the monopolar case electrode, in order to control the polarity, amplitude, rate, pulse width and channel through which the current stimulus pulses are provided. Other output circuits can be used with the invention, including voltage regulated output, multiplexed channels, and the like.

As shown in FIG. 3, much of circuitry included within the IPG 100 may be realized on a single application specific integrated circuit (ASIC) 190. This allows the overall size of the IPG 100 to be quite small, and readily housed within a suitable hermetically-sealed case. The IPG 100 includes n feedthroughs to allow electrical contact to be individually made from inside of the hermetically-sealed case with the n electrodes that form part of the lead system outside of the case. The IPG case is preferably made from titanium and is shaped in a rounded case, as illustrated, e.g., in FIG. 2. The rounded IPG case has a maximum circular diameter D of about 50 mm, and preferably only about 45 mm (or equivalent area). The implant case has smooth curved transitions that minimize or eliminate edges or sharp corners. The maximum thickness W of the case is about 10 mm. Other materials, e.g. ceramic, can be used that provide less shielding between the recharging coils, and thus improving efficiency.

Figure 4:
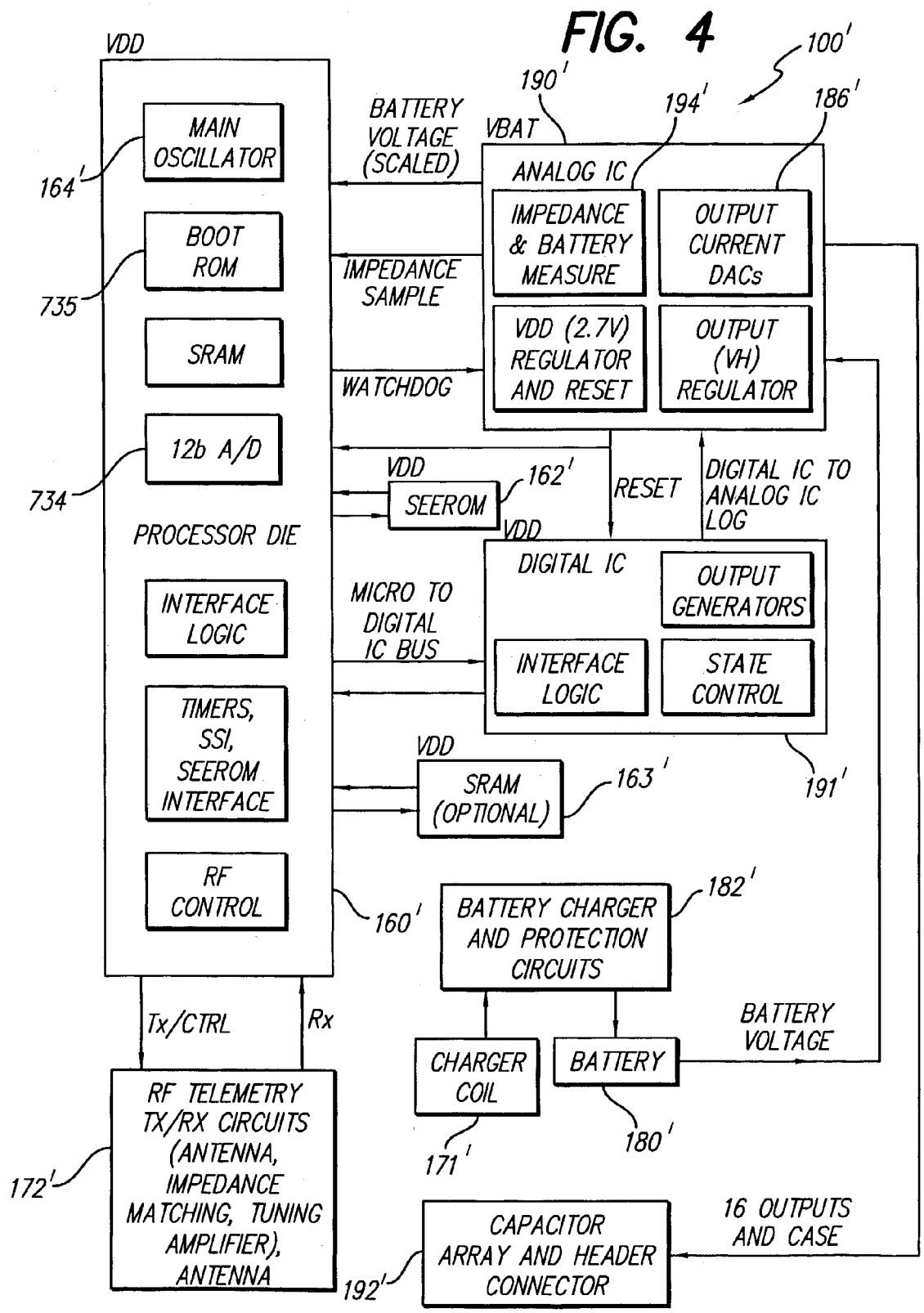
FIG. 4 is a block diagram that illustrates another embodiment of an implantable pulse generator (IPG) that may be used with the invention.

It is thus seen that the implant portion 10 of the SCS system of the present invention (see FIG. 1) includes an implantable pulse generator (IPG) 100 with a rechargeable battery 180 as described in FIG. 4. Such IPG further includes stimulating electronics (comprising programmable current sources and a switching matrix and associated control logic), and a telemetry system. Advantageously, the rechargeable battery 180 may be recharged repeatedly as needed.

In use, the IPG 100 is placed in a surgically-made pocket either in the abdomen, or just at the top of the buttocks, and detachably connected to the lead system (comprising lead extension 120 and electrode array 110). While the lead system is intended to be permanent, the IPG may be replaced should its power source fail, or for other reasons. Thus, a suitable connector, e.g., the snap-on tool-less connector disclosed in U.S. patent application Ser. No. 09/239,926, filed Jan. 28, 1999, or other suitable connectors, may advantageously be used to make the connection between the lead system and the IPG 100. This '926 patent application is incorporated herein by reference.

Once the IPG 100 has been implanted, and the implant system 10 is in place, the system is programmed to provide a desired stimulation pattern at desired times of the day. The stimulation parameters that can be programmed include the number of channels (defined by the selection of electrodes with synchronized stimulation), the stimulation rate and the stimulation pulse width. The current output from each electrode is defined by polarity and amplitude.

The back telemetry features of the IPG 100 allow the status of the IPG to be checked. For example, when the external hand-held programmer 202 (and/or the clinician programmer 204), initiates a programming session with the implant system 10 (FIG. 1), the capacity of the battery is telemetered so that the external programmer can calculate the estimated time to recharge. Any changes made to the current stimulus parameters are confirmed through back telemetry, thereby assuring that such changes have been correctly received and implemented within the implant system. Moreover, upon interrogation by the external programmer, all programmable settings stored within the implant system 10 may be uploaded to one or more external programmers.

Turning next to FIG. 4, a hybrid block diagram of an alternative embodiment of an IPG 100' that may be used with the invention is illustrated. The IPG 100' includes both analog and digital dies, or integrated circuits (IC's), housed in a single hermetically-sealed rounded case having a diameter of about 45 mm and a maximum thickness of about 10 mm. Many of the circuits contained within the IPG 100' are identical or similar to the circuits contained within the IPG 100, shown in FIG. 3. The IPG 100' includes a processor die, or chip, 160', an RF telemetry circuit 172' (typically realized with discrete components), a charger coil 171', a lithium ion or lithium ion polymer battery 180, battery charger and protection circuits 182', memory circuits 162' (SEEROM) and 163' (SRAM), a digital IC 191', an analog IC 190', and a capacitor array and header connector 192'.

The capacitor array and header connector 192' includes 16 output decoupling capacitors, as well as respective feedthrough connectors for connecting one side of each decoupling capacitor through the hermetically-sealed case to a connector to which the electrode array 110, or lead extension 120, may be detachably connected.

The processor 160' is realized with an application specific integrated circuit (ASIC) that comprises the main device for full bidirectional communication and programming. The processor 160' utilizes a 8086 core (the 8086 is a commercially-available microprocessor available from, e.g., Intel, or a low power equivalent thereof, 16 kilobytes of SRAM memory, two synchronous serial interface circuits, a serial EEPROM interface, and a ROM boot loader 735. The processor die 160' further includes an efficient clock oscillator circuit 164' and a mixer and modulator/demodulator circuit implementing the QFAST RF telemetry method supporting bi-directional telemetry at 8 Kbits/second. QFAST stands for "Quadrature Fast Acquisition Spread Spectrum Technique", and represents a known and viable approach for modulating and demodulating data. The QFAST RF telemetry method is further disclosed in U.S. Pat. No. 5,559,828, incorporated herein by reference. An analog-to-digital converter (A/D) circuit 734 is also resident on the processor 160' to allow monitoring of various system level analog signals, impedances, regulator status and battery voltage. In the preferred embodiment, the A/D converter circuit 734 comprises a twelve-bit A/D converter. The processor 160' further includes the necessary communication links to other individual ASIC's utilized within the IPG 100'. The processor 160', like all similar processors, operates in accordance with a program that is stored within its memory circuits.

The analog IC (AIC) 190' comprises an ASIC that functions as the main integrated circuit that performs several tasks necessary for the functionality of the IPG 100', including providing power regulation, stimulus output, and impedance measurement and monitoring. Electronic circuitry 194' performs the impedance measurement and monitoring function. The main area of the analog 190' is devoted to the current stimulus generators 186'. These generators 186' may be realized using the circuitry described in the previously-referenced patent application, or similar circuitry. These generators 186' are designed to deliver up to 20 mA aggregate and up to 12.7 mA on a single channel in 0.1 mA steps, which resolution requires that a seven (7) bit digital-to-analog (DAC) circuit be employed at the output current DAC 186'. Regulators for the IPG 100' supply the processor and the digital sequencer with a voltage of 2.7 V±10%. Digital interface circuits residing on the AIC 190' are similarly supplied with a voltage of 2.7 V±10%. A regulator programmable from 5V to 18V supplies the operating voltage for the output current DACs 186'. The output current sources on the analog IC thus include sixteen bidirectional output current sources, each configured to operate as a DAC current source. Each DAC output current source may source or sink current, i.e., each DAC output current source is bidirectional. Each DAC output current source is connected to an electrode node. Each electrode node, in turn, is connected to a coupling capacitor Cn. The coupling capacitors Cn and electrode nodes, as well as the remaining circuitry on the analog IC 186', are all housed within the hermetically sealed case of the IPG 100. A feedthrough pin, which is included as part of the header connector 192', allows electrical connection to be made between each of the coupling capacitors Cn and the respective electrodes E1, E2, E3, . . . or E16, to which the DAC output current source is associated.

The digital IC (DigIC) 191' functions as the primary interface between the processor 160' and the AIC output circuits 186'. The main function of the DigIC 191' is to provide stimulus information to the output current generator register banks. The DigIC 191' thus controls and changes the stimulus levels and sequences when prompted by the processor 160'. In a preferred embodiment, the DigIC 191' comprises a digital application specific integrated circuit (digital ASIC).

The RF circuitry 172' includes antennas and preamplifiers that receive signals from the HHP 202 and provide an interface at adequate levels for the demodulation/modulation of the communication frames used in the processor 160'. Any suitable carrier frequency may be used for such communications. In a preferred embodiment, the frequency of the RF carrier signal used for such communications is 262.144 KHz, or approximately 262 KHz. A transmitter section receives digital transmit signals from the quadrature components, TxI and TxQ, of the data as generated on the 262 KHz carrier. The TxI and TxQ signals are coupled directly into the antenna during transmit. Additionally, the transmit section couples the antenna to the receiver during a receive mode. The transmitter section is responsible for antenna tunning and coupling while minimizing the processor noise to the RF signal. Appendix B contains additional information regarding the RF communications that occur between the IPG and external devices, e.g., the handheld programmer 202.

A receiver portion of the RF circuitry 172' receives an incoming RF signal through a coupling circuit, amplifies the signal, and delivers it to a mixer located inside of the processor 160'.

The RF circuitry 172' also includes an antenna. The antenna, in a preferred embodiment, comprises a ferrite rod located in an epoxy header of the IPG case. The antenna makes electrical connection to the IPG circuitry via two feedthrough pins included within the header connector 192'

(the other pins providing electrical connection to the individual electrodes located in the electrode array 110).

The Battery Charger and Protection Circuits 182' provide battery charging and protection functions for the Lithium Ion battery 180. A charger coil 171' inductively (i.e., electromagnetically) receives rf energy from the external charging station. The battery 180 preferably has a 720 mWHr capacity. The preferred battery 180 has a life of 500 cycles over 10 years with no more than 80% loss in capacity. The battery charger circuits perform three main functions: (1) during normal operation, they continually monitor the battery voltage and provide charge status information to the patient at the onset of a communication link, (2) they ensure that the battery is not over-discharged, and (3) they monitor the battery voltage during a charging cycle to ensure that the battery does not experience overcharging. These functions are explained in more detail below in conjunction with FIGS. 7, 8 and 9.

Figure 5:
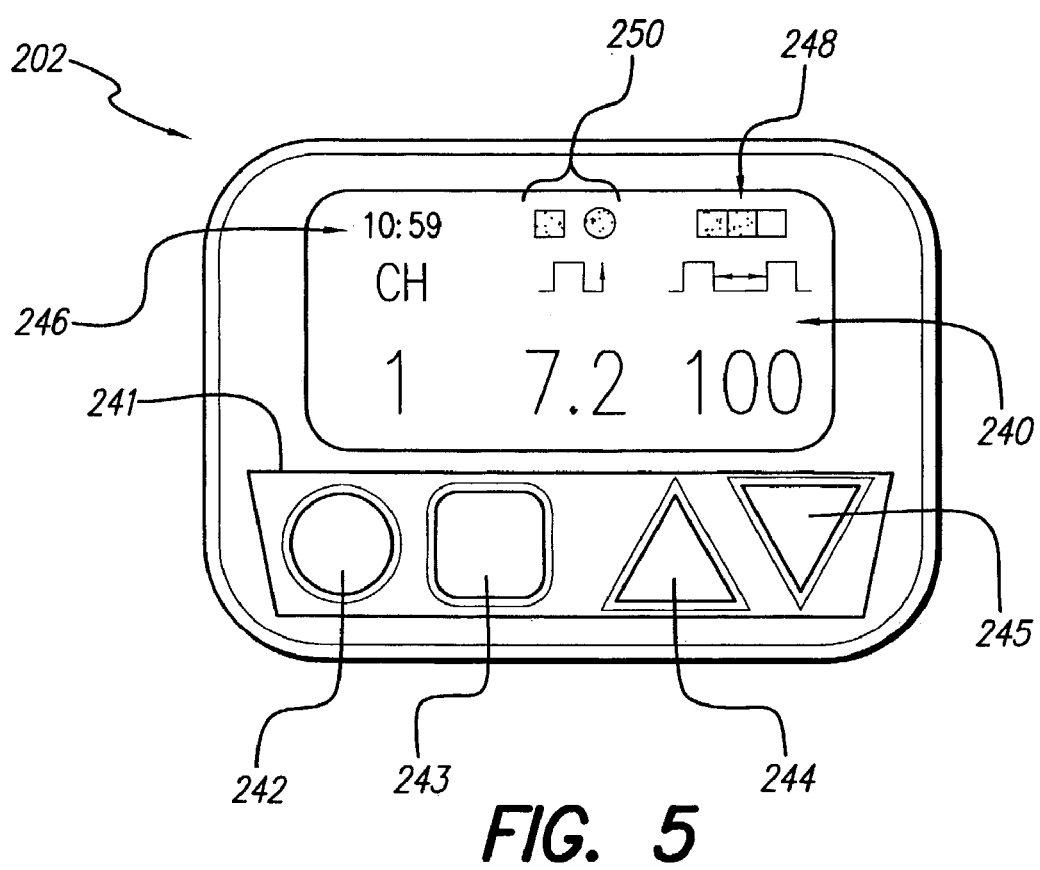
FIG. 5 shows a representative screen on a handheld patient programmer that may be used with the invention.

Next, a representation of one embodiment of the HHP 202 is shown in FIG. 5. As seen in FIG. 5, the HHP includes a lighted display screen 240 and a button pad 241 that includes a series of buttons 242, 243, 244 and 245. (The number of buttons shown in FIG. 5 is exemplary only; any number of buttons may be employed.) The buttons provided within the button pad 241 allow the IPG to be tuned ON or OFF, provide for the adjustment or setting of up to three parameters at any given time, and provide for the selection between channels or screens. Some functions or screens may be accessible by pressing particular buttons in combination or for extended periods of time. In a preferred embodiment, the screen 240 is realized using a dot matrix type graphics display with 55 rows and 128 columns.

The button pad 241, in a preferred embodiment, comprises a membrane switch with metal domes positioned over a flex circuit, which bonds to the top housing of the HHP. A keypad connector connects directly a printed circuit board (PCB) of the HHP, and the bonding to the housing seals the connector opening.

In a preferred embodiment, the patient handheld programmer 202 is turned ON by pressing any button, and is automatically turned OFF after a designated duration of disuse, e.g., 1 minute. One of the buttons, e.g., the IPG button 242, functions as an ON-OFF button for immediate access to turn the IPG on and off. When the IPG is turned ON, all channels are turned on to their last settings. If slow start/end is enabled, the stimulation intensity is ramped up gradually when the IPG (or ETS) is first turned ON with the HHP. When the IPG is turned OFF, all channels are turned off. If slow start/end is enabled, the stimulation intensity may be ramped down gradually rather than abruptly turned off. Another of the buttons, e.g., the SEL button 243, functions as a "select" button that allows the handheld programmer to switch between screen displays and/or parameters. Up/down buttons 244 and 245 provide immediate access to any of three parameters, e.g., amplitude, pulse width, and rate.

Also included on the screens shown on the display 240 of the handheld programmer 202 are status icons or other informational displays. A battery recharge countdown number 246 shows the estimated time left before the battery of the IPG needs to be recharged. A battery status icon 248 further shows or displays the estimated implant battery capacity. This icon flashes (or otherwise changes in some fashion) in order to alert the users when a low battery condition is sensed. Every time the patient programmer is activated to program or turn on the IPG, the actual battery status of the implanted pulse generator (IPG) is interrogated and retrieved by telemetry to reconcile actual verses estimated battery capacity. Other status icons 250 are provided that display the status of the patient-programmer-to-implant link and the patient-programmer-to-clinician-programmer link.

As a safety feature, the physician may lock out or set selectable parameter ranges via the fitting station to prevent the patient from accessing undesirable settings (i.e., a lockout range). Typically, locked parameters are dropped from the screen display.

The main screen displayed by default upon activation of the handheld programmer 202 shows amplitude and rate by channel, as illustrated in FIG. 5. As shown in FIG. 5, the display is for channel 1, the amplitude is 7.2 ma, and the rate is 100 pps. Thus, it is seen that the channel number (or abbreviated channel name as set by the clinician programmer) is displayed on the screen with the parameters. Amplitude is the preferred default selection (i.e., it is the parameter that is displayed when the unit is first turned ON).

Whenever a displayed parameter is changed, the settings of the IPG 100 are changed via telemetry to reflect the change. However, in order to assure that the IPG has received the telemetry signal and made the corresponding change without a discrepancy between the IPG and the value displayed, a back telemetry response must be received from the IPG before the screen value changes. Only the parameters that have not been locked out from the clinician's programming station are adjustable. Further, only those channels that have electrodes programmed for stimulation are selectable.

Figure 6:
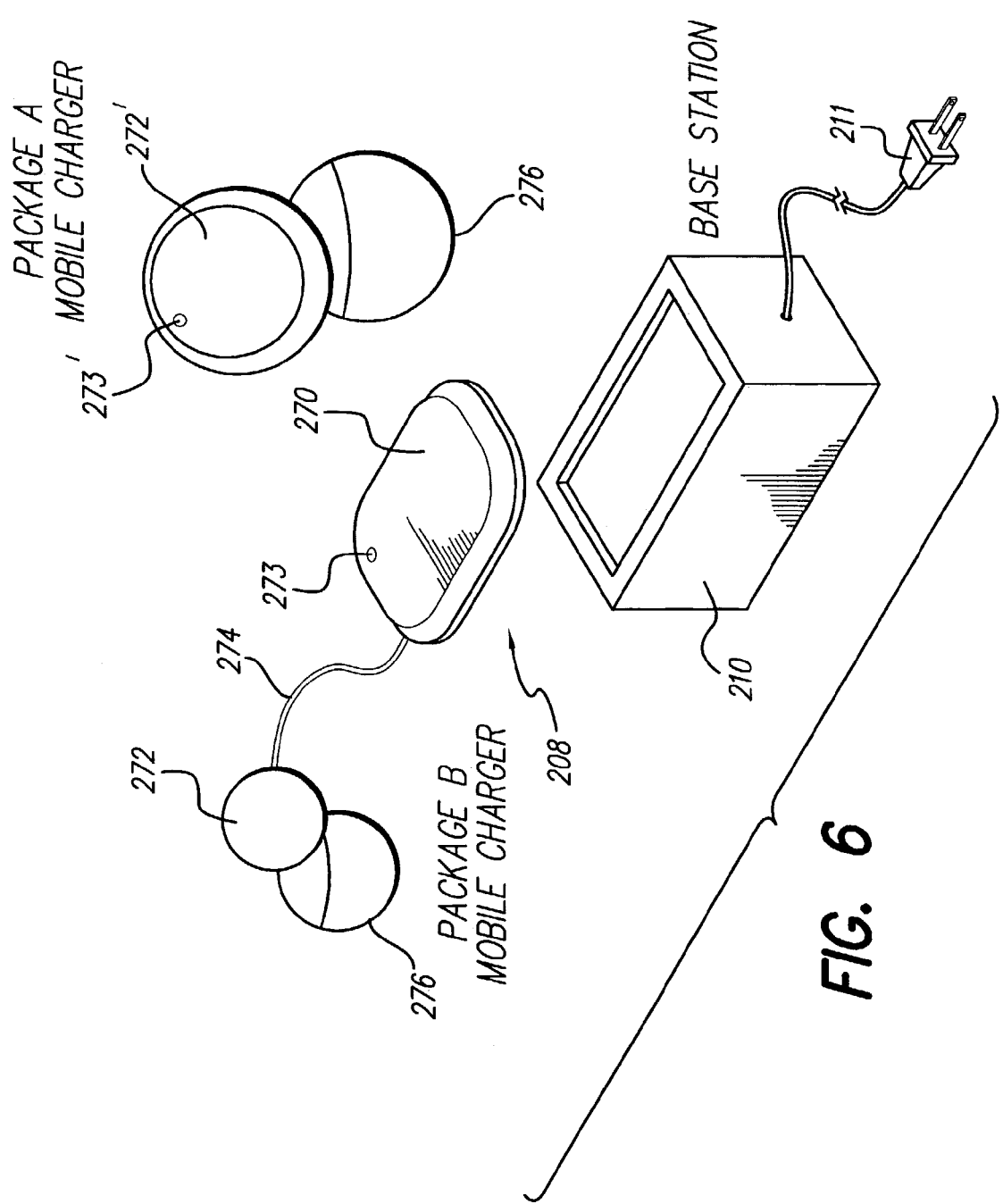
FIG. 6 illustrates the external components of a representative portable charging system used by the invention.
Figure 8:
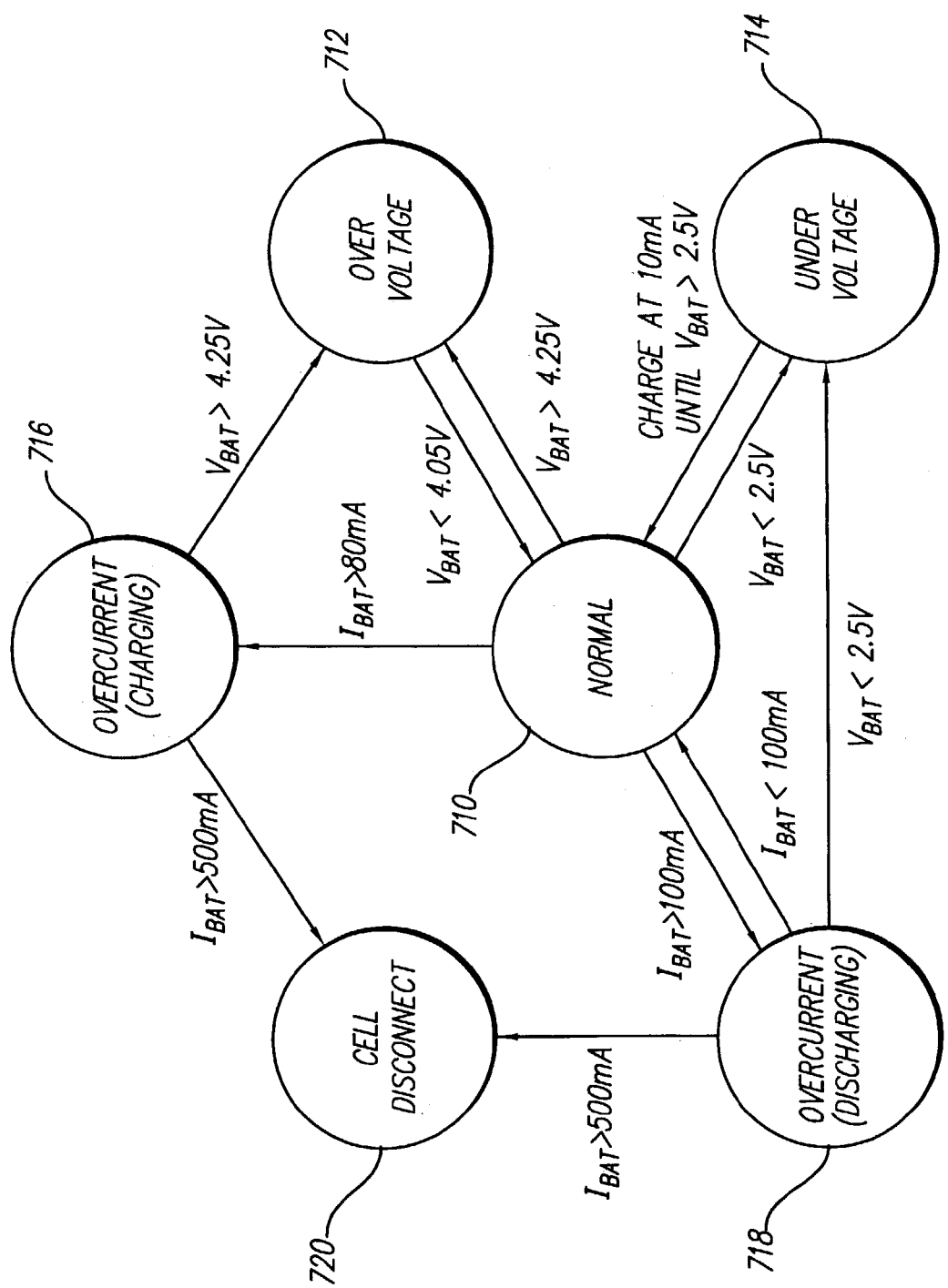
FIG. 8 is a state diagram illustrating the various states that may be assumed by the implant battery charging circuitry during operation of the charging system.

Turning next to FIG. 6, the external components of a representative portable charging system used with the invention are illustrated. The recharging system is used to transcutaneously recharge the implant battery 180 of the IPG 100 as needed, via inductive coupling. Recharging typically occurs at a rate of approximately C/2 (current equal to one-half battery capacity). In order to recharge the battery from a completely discharged state to 80% capacity, approximately two hours recharge time is required. Because of this time, a portable charger system is preferred. Hence, as seen in FIG. 8, a two part system is preferred comprising a portable charger 208 and a base station 210. The base station 210 is connected to an AC plug 211, and may thus be easily plugged into any standard 110 VAC outlet. The portable charger 208 includes recharging circuitry housed within a housing 270 that may be detachably inserted into the charging port 210 in order to be recharged. Thus, both the IPG 100 and the portable charger 208 are rechargeable. The housing 270 is returned to the charging port 210 between uses.

For the "Package B" embodiment shown in FIG. 6, a charging head 272 is connected to the recharging circuitry 270 by way of a suitable flexible cable 274. When the IPG battery needs to be recharged, a disposable adhesive pouch 276, double sided adhesive, or a Velcro® strip is placed on the patient's skin, over the location where the IPG is implanted. For patients with adhesive allergies, a flexible belt with an attachment means for the charger is provided such that the patient can secure the charger over the implant. The charging head 272 is then simply slid into the pouch, adhered to the adhesive, or fastened to the strip, so that it is within 2–3 cm of the IPG 100.

In order for efficient transfer of energy to the IPG, it is important that the head 272 (or more particularly, the coil within the head 272) be properly aligned with the IPG. Thus, in a preferred embodiment, a speaker generates an audio tone when the two devices are not aligned, or misaligned.

The misalignment indicator is activated by sensing a change in the charge coil voltage, which reflects a change in the reflected impedance, as discussed in more detail below. When the coil voltage is greater than a predetermined value, a beeping or other audible tone and/or visual indicator is activated. When the coil voltage drops below this value, the beeping or tone or visual indicator turns off. The advantage of such a feature is that should the device move out of range of the implant (more likely with a non-adhesive attachment mechanism), the misalignment indicator is activated resulting in a beeping sound or other recognizable indicator so that the patient is immediately informed to readjust the position of the charging device. A misalignment indicator may also be implemented in visual form, such as a light emitting diode (LED).

The external charging device also has a state of charge indicator, i.e. an LED, or an audio tone, to indicate when the external battery is fully charged. This feature can also be included in a primary battery operated charger, so that a new battery is required for each charge session. When charging the implant, the charger battery would be depleted. A charge completion indicator is also provided such that when the charger battery is nearly depleted, a distinct tone is generated to alert the user. Also, back-telemetry with the IPG allows the charging process to be monitored. When the implant battery is fully charged, a signal will be communicated from the implant to the charger, and a distinct audio tone will be generated to alert the user.

An alternative embodiment of the portable charger 208 includes the recharging circuitry and battery and charging head housed within a single round or oval shaped package 272, as also shown in FIG. 6 (labeled "Package A"). Such package is approximately three inches in diameter and is comfortable to hold against the skin. The adhesive pouch 276 need not necessarily comprise a pouch, but may utilize any suitable means for holding the head (coil) of the charger 208 in proper alignment with the IPG, such as Velcro® strips or adhesive patches.

Figure 7A:
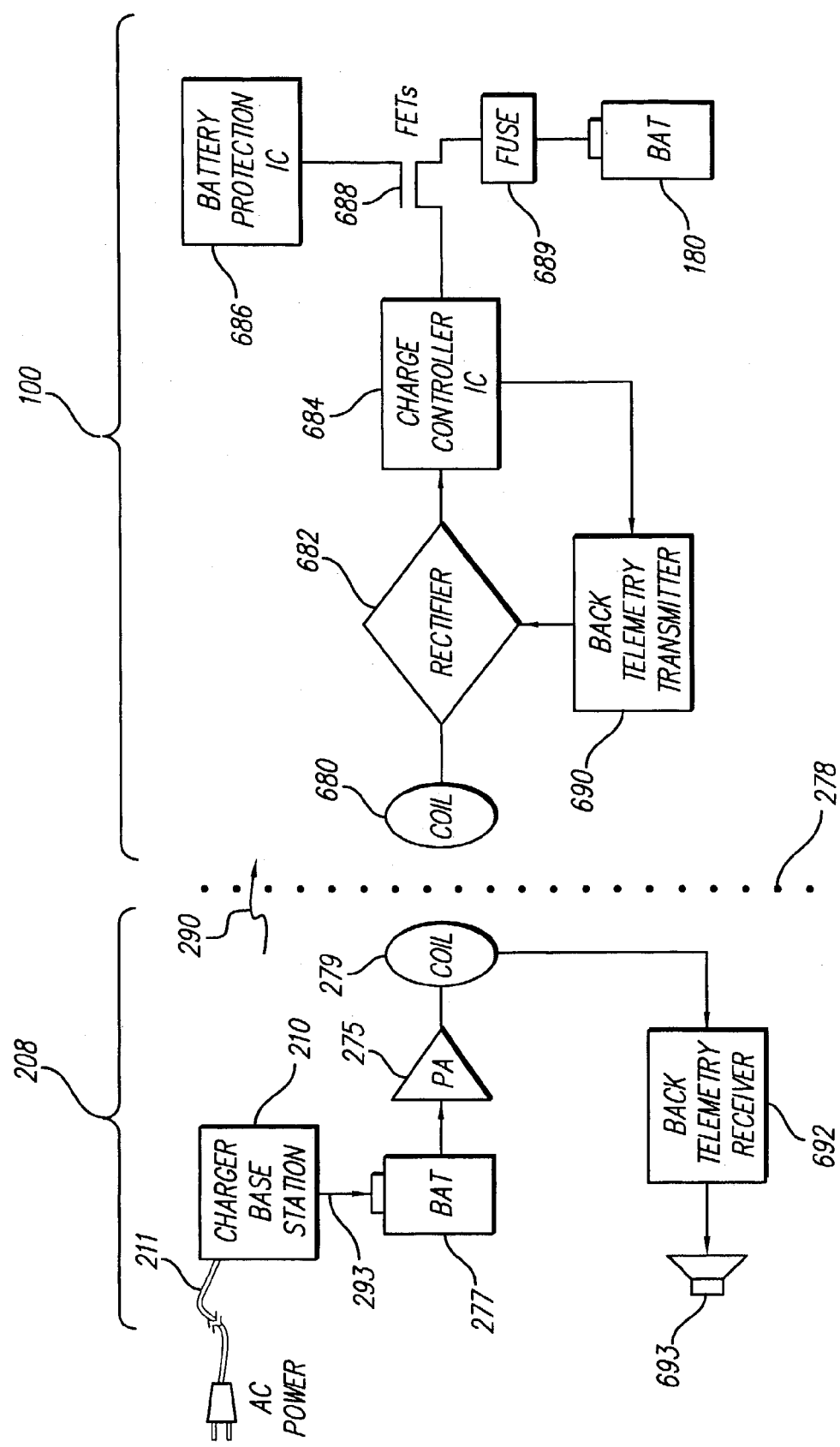
FIG. 7A shows a block diagram of the battery charging system used with the invention.

Turning next to FIG. 7A, a block diagram of the recharging elements of the invention is illustrated. As shown in FIG. 7A, (and as also evident in FIGS. 3 and 4), the IPG 100 is implanted under the patient's skin 278. The IPG includes a replenishable power source 180, such as a rechargeable battery. It is this replenishable power source that must be replenished or recharged on a regular basis, or as needed, so that the IPG 100 can carry out its intended function. To that end, the recharging system of the present invention uses the portable external charger 208 to couple energy, represented in FIG. 7A by the wavy arrow 290, into the IPG's power source 180. The portable external charger 208, in turn, obtains the energy 290 that it couples into the power source 180 from its own battery 277.

The battery 277 in the charger 208, in the preferred embodiment, comprises a rechargeable battery, preferably a Lithium-Ion battery or a lithium-ion polymer battery. (Alternatively, the battery 277 may comprise a replaceable battery.) When a recharge is needed, energy 293 is coupled to the battery 277 via the charging base station 210 in conventional manner. The charging base station 210, in turn, receives the energy it couples to the battery 277 from an AC power line 211. A power amplifier 275, included within the portable charger 208, enables the transfer of energy from the battery 277 to the implant power source 180. Such circuitry 275 essentially comprises DC-to-AC conversion circuitry that converts dc power from the battery 277 to an ac signal that may be inductively coupled through a coil 279 located in the external charging head 272 (or within the round case 272', see FIG. 6) with another coil 680 included within the IPG 100, as is known in the art. Upon receipt of such ac signal within the IPG 100, it is rectified by rectifier circuitry 682 and converted back to a dc signal which is used to replenish the power source 180 of the implant through a charge controller IC 684. A battery protection IC 686 controls a FET switch 688 to make sure the battery 180 is charged at the proper rate, and is not overcharged. A fuse 689 also protects the battery 180 from being charged with too much current. The fuse 689 also protects from an excessive discharge in the event of an external short circuit.

Thus, from FIG. 7A, it is seen that the battery charging system consists of external charger circuitry 208, used on an as-needed basis, and implantable circuitry contained within the IPG 100. In the charger 208, the rechargeable Lithium-ion battery 277 (recharged through the base station 210), or equivalent, provides a voltage source for the power amplifier 275 to drive the primary coil 279 at a resonant frequency. The secondary coil 680, in the IPG 100, is tuned to the same resonant frequency, and the induced AC voltage is converted to a DC voltage by rectifier circuit 682. In a preferred embodiment, the rectifier circuit 682 comprises a bridge rectifier circuit. The charge controller IC 684 coverts the induced power into the proper charge current and voltage for the battery. The battery protection IC 686, with its FET switch 688, is in series with the charge controller 684, and keeps the battery within safe operating limits. Should an overvoltage, undervoltage, or short-circuit condition be detected, the battery 180 is disconnected from the fault. The fuse 689 in series with the battery 180 provides additional overcurrent protection. Charge completion detection is achieved by a backtelemetry transmitter 690, which transmitter modulates the secondary load by changing the full-wave rectifier into a half-wave rectifier/voltage clamp. This modulation is, in turn, sensed in the charger 208 as a change in the coil voltage due to the change in the reflected impedance. When detected, an audible alarm is generated through a back telemetry receiver 692 and speaker 693. Reflected impedance due to secondary loading is also used to indicate charger/IPG alignment, as explained in more detail below in conjunction with the description of FIG. 9.

In a preferred embodiment, and still with reference to FIG. 7A, the charge coil 680 comprises a 36 turn, single layer, 30 AWG copper air-core coil, and has a typical inductance of 45 µH and a DC resistance of about 1.15 ohms. The coil 680 is tuned for resonance at 80 KHz with a parallel capacitor. The rectifier 682 comprises a full-wave (bridge) rectifier consisting of four Schottky diodes. The charge controller IC 684 comprises an off-the-shelf, linear regulation battery charger IC available from Linear Technology as part number LTC1731-4.1. Such charger is configured to regulate the battery voltage to 4.1 VDC. When the induced DC voltage is greater than 4.1 VDC (plus a 54 mV dropout voltage), the charge controller 684 outputs a fixed constant current of up to 80 mA, followed by a constant voltage of 4.1±0.05 V. If insufficient power is received for charging at the maximum rate of 80 mA, the charge controller 684 reduces the charge current so that charging can continue. Should the battery voltage fall below 2.5 V, the battery is trickled charged at 10 mA. The charge controller 684 is capable of recharging a battery that has been completely discharged to zero volts. When the charge current drops to 10% of the full-scale charge current, or 8 mA, during the constant voltage phase, an output flag is set to signal that charging has completed. This flag is used to gate the oscillator output for modulating the rectifier configuration (full-wave to half-wave), which change in rectifier configuration is sensed by the external charging circuit to indicate charge completion.

The battery protection IC 686, in the preferred embodiment, comprises an off-the-shelf IC available from Motorola as part number MC33349N-3R1. This IC monitors the voltage and current of the implant battery 180 to ensure safe operation. Should the battery voltage rise above a safe maximum voltage, then the battery protection IC 686 opens the charge-enabling FET switches 688 to prevent further charging. Should the battery voltage drop below a safe minimum voltage, or should the charging current exceed a safe maximum charging current, the battery protection IC 686 prevents further discharge of the battery by turning off the charge-enabling FET switches 688. In addition, as an additional safeguard, the fuse 689 disconnects the battery 180 if the battery charging current exceeds 500 mA for at least one second.

Figure 9:
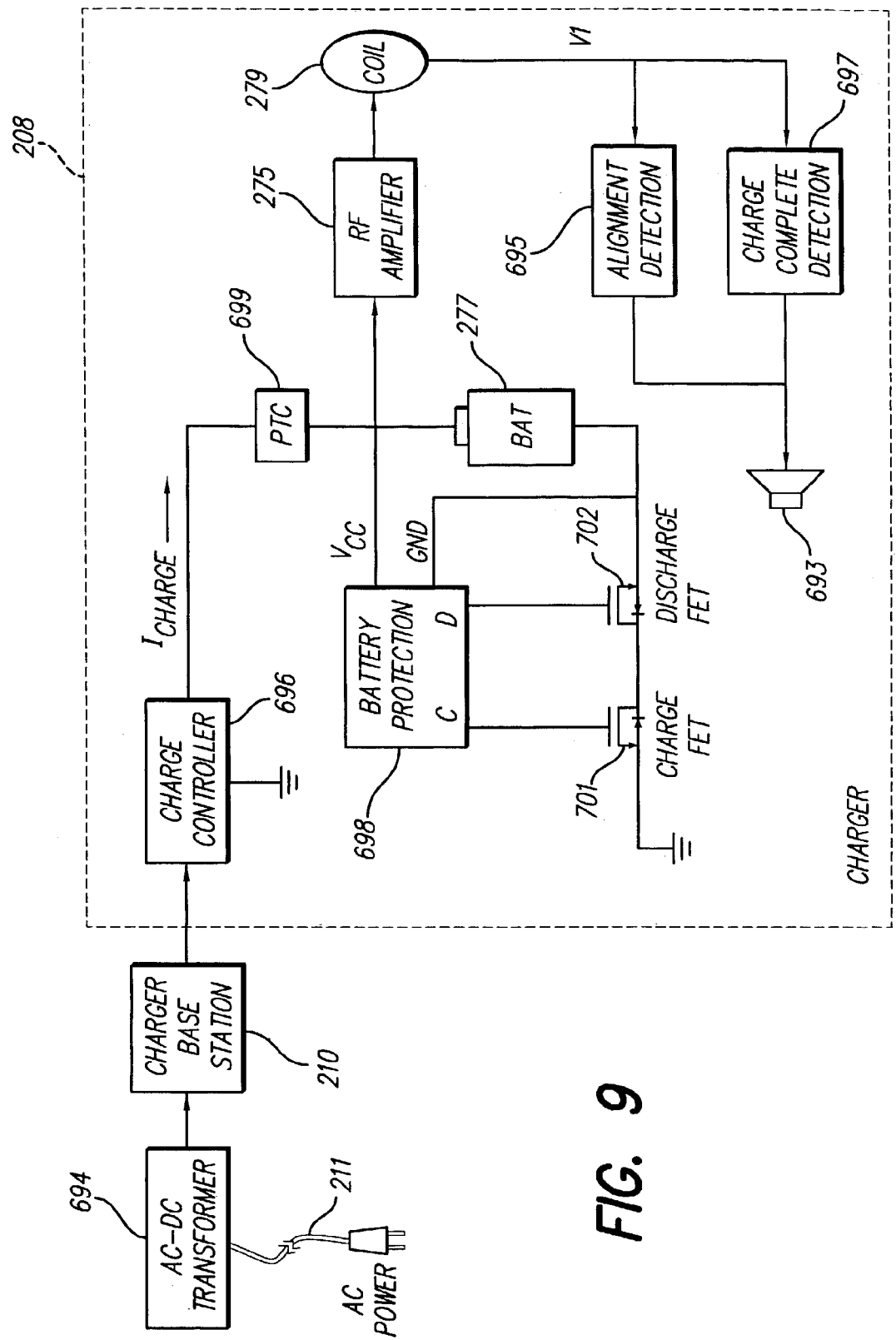
FIG. 9 shows a block diagram of the battery charger/protection circuitry utilized within the external charging station of the invention.

In a preferred embodiment, the charge-enabling FET switches 688 comprise a Charge FET and a Discharge FET connected in series similar to the FETs 701 and 701 shown in FIG. 9. In the event of a sensed malfunction, the protection IC 686 switches off the battery 180 by turning off one of the two FET switches 688. If the battery voltage is greater than a predetermined value, the Charge FET is turned off to block further charging. Conversely, if the battery voltage is less than a predetermined value, the Discharge FET turns off to block further discharging. If the battery voltage is zero, both the Charge FET and the Discharge FET turn off since the Battery Protection circuit is powered directly from the battery. Only when a charge voltage greater than $V_{GS}$, or the gate-source threshold voltage, of the Charge FET is applied (which is approximately 1.5 volts) will charging resume at a rate lower than normal charging, i.e., 10% fo the normal rate, until the voltage has reached a predetermined level.

Figure 7B:
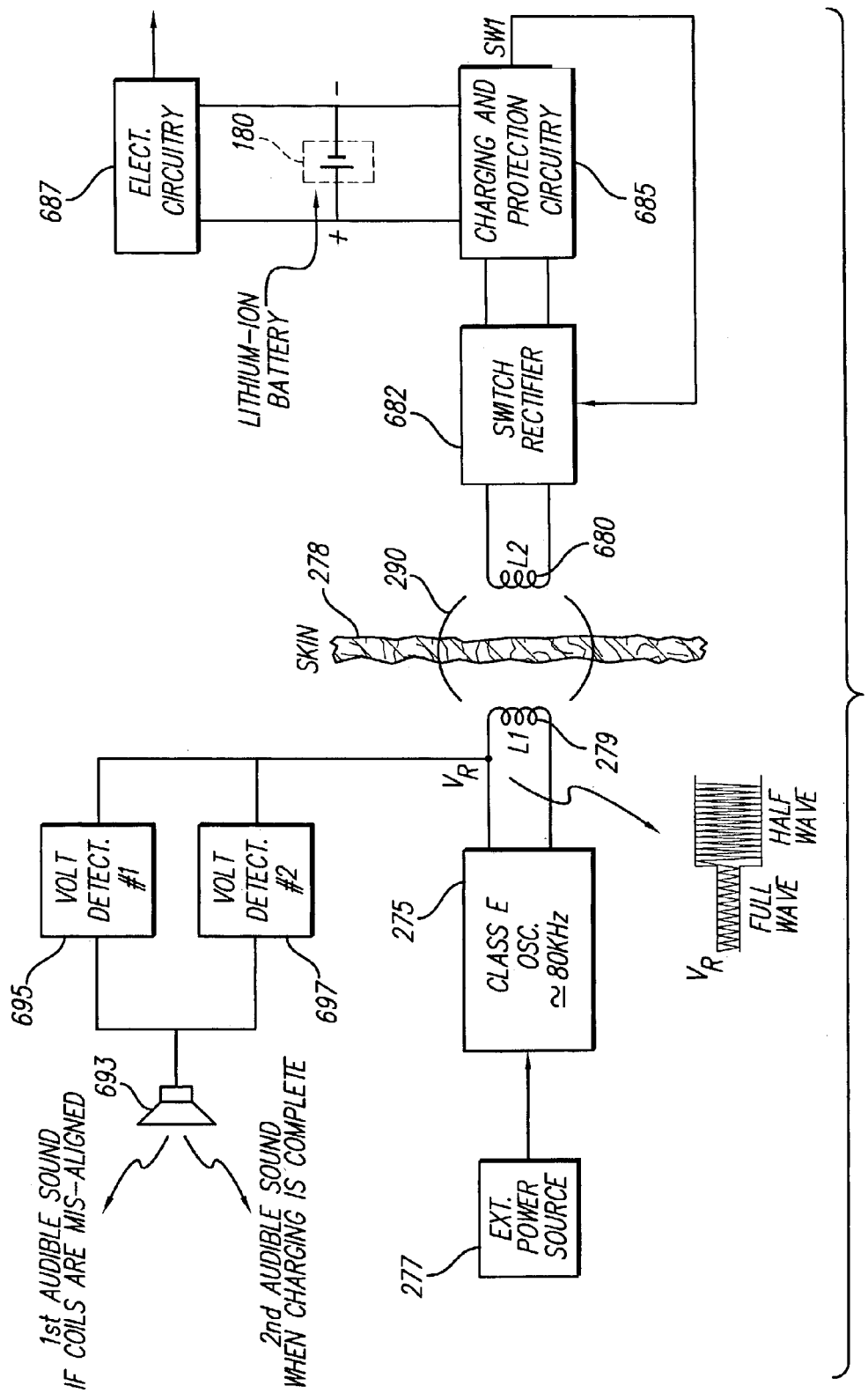
FIG. 7B is a functional block diagram of the preferred misalignment and charge complete indicators used with the invention.

Turning next to FIG. 7B, a summary of the preferred misalignment detection circuitry and charge completion detection circuitry used by the invention is illustrated. As seen in FIG. 7B, an external power source 277, e.g., a rechargeable or replaceable battery, drives a class E oscillator 275, which applies an ac signal, e.g., a signal of about 80 KHz, to the primary coil 279, which coil is also labeled L1 in FIG. 7B. The voltage $V_R$ at the coil L1 is monitored by a first voltage detection circuit 695 and by a second voltage detection circuit 697. Both of the voltage detection circuits 695 and 697 are connected to a speaker 693, or equivalent audible-tone generator.

The coil L1 couples energy 290 through the skin 278 of the user to an implanted coil L2 (also referred to as coil 680) that is part of the implanted device. The coil L2 inductively (electromagnetically) receives the ac signal 290. That is, the ac signal 290 is induced in the coil L2 as a result of the alternating magnetic field that is created when the signal is applied to the external coil L1. The alternating signal received at coil L2 is rectified by the switch regulator 682, thereby creating a dc voltage that is applied to charging and protection circuitry 685 for delivery to the implanted rechargeable battery 180. The battery 180, in turn, provides operating power for the electronic circuitry 687 included within the implant device so that such device may carry out its intended function, e.g., provide stimulation pulses through implanted electrodes to desired nerves or body tissue. The circuitry 685 controls how much charging current is applied to the battery 180 and monitors the battery voltage. The switch regulator 682 operates as either a full-wave rectifier circuit or a half-wave rectifier circuit as controlled by a control signal SW1 generated by the charging and protection circuitry 685.

In normal operation, that is, when the battery 180 has been depleted and is receiving a charge, the switch rectifier 682 operates as a full-wave rectifier circuit. During this time, assuming that the coils L1 and L2 are properly aligned, the voltage $V_R$ sensed by voltage detector 695 is at a minimum level because a maximum energy transfer is taking place. Should the coils L1 and L2 become misaligned, then less than a maximum energy transfer occurs, and the voltage $V_R$ monitored by detection circuit 695 significantly increases. If the voltage $V_R$ is greater than a prescribed threshold level, then voltage detection circuit 695 causes the speaker 693 to emit a fist audible sound, which first audible sound indicates a misaligned condition. As soon as the coils L1 and L2 are placed in proper alignment, an optimum energy transfer condition is established, causing the voltage $V_R$ to decrease below the threshold, thereby causing the detection circuit 695 to cease emitting the first audible sound. In this manner, then, it is seen that the detection circuit 695 operates as a misalignment detector, providing audible feedback as to when a misaligned condition between the coils L1 and L2 is present. Visual feedback could also be provided, if desired.

As the battery 180 continues to be charged, the charging and protection circuitry continue to monitor the charge current and battery voltage. When the charge current and battery voltage reach prescribed levels, which prescribed levels are indicative of a fully charged battery, the signal SW1 is generated by the charging and protection circuitry 685. The signal SW1, in turn, causes the switch rectifier circuit 682 to switch to half-wave rectifier operation. When this change occurs, the voltage $V_R$ sensed by voltage detector 697 suddenly changes from a minimal peak-to-peak amplitude to a larger peak-to-peak amplitude, as shown in FIG. 7B. The detector 697 is adapted to sense this sudden transient or pulsed change in amplitude, and in response thereto causes a 2nd audible sound, e.g., a beeping sound, to be generated through the speaker 693. This second audible sound thus signals the user that the battery is fully charged. Visual feedback could be used in lieu of, or in addition to, the 2nd audible sound, if desired.

It is noted that the operation of the misalignment and full-charge detection circuits, illustrated in FIG. 7B, operate without the use of conventional rf backtelemetry signals being sent from the implanted device to an external device. In practice, such conventional backtelemetry rf signals may be used to signal the hand held programmer (HHP), when placed in telecommunicative contact with the implanted device, in order to provide a status report regarding the state of the charge of the battery 180 or other conditions within the implant device. However, it should be noted that the switch rectifier 682 may be modulated, by switching back and forth between full-wave and half-wave conditions, in order to create data words in the modulation pattern of the voltage $V_R$ that may be sensed and decoded at the external device, thereby providing a means for backtelemetry communication without using conventional rf signal generation, modulation, and transmission.

Next, with reference to FIG. 8, a state diagram that shows the various charging states that may occur in a preferred embodiment of the invention relative to the implant battery 180 is shown. As seen in FIG. 8, and assuming a preferred lithium-ion or lithium-ion polymer battery is used, a normal state 710 reflects that the battery voltage and charging current are within appropriate limits. An over voltage state 712 exists when the battery voltage is greater than about 4.25 V and continues to exist until the battery voltage is less than about 4.05 V. An undervoltage state 714 exists when the battery voltage is less than 2.5 volts. The undervoltage state 714 continues to exist until the battery voltage is greater than 2.5 volts while charging at a prescribed trickle charge current, e.g., 10 mA. An overcurrent (charging) state 716 exists whenever the charging current exceeds 80 mA. If, while in the overcurrent (charging) state 716, the battery voltage is greater than 4.25 volts, then the over voltage state 712 is entered. If, while in the overcurrent (charging) state 716, the charging current exceeds 500 mA for more than one minute, the fuse 689 opens, and a cell disconnect state 720 is permanently entered. An overcurrent (discharging) state 718 is entered whenever the battery charging current is greater than 100 mA, and continues until the battery charging current is less than 100 mA. If, while in the overcurrent (discharging) state 718, the battery voltage drops below 2.5 volts, then the under voltage state 714 is entered. Also, should the battery current exceed 500 mA for more than one minute while in the overcurrent (discharging) state 718, the fuse 689 opens, and the cell disconnect state 720 is permanently entered.

Thus, it is seen that through operation of the states shown in FIG. 8, the rechargeable battery 180 is fully protected from all conditions—overvoltage, undervoltage, overcharge, and undercharge—that may exist and which could potentially damage the battery or shorten its operating life.

Turning next to FIG. 9, a block diagram of the preferred circuitry within the external charging station 208 is shown. The charging station comprises a portable, non-invasive transcutaneous energy transmission system designed to fully charge the implant battery in under three hours (80% charge in two hours). Energy for charging the IPG battery 180 initially comes from the main supply line 211, and is converted to 5 VDC by an AC–DC transformer 694, which 5 VDC proves the proper supply voltage for the charger base station 210. When the charger 208 is placed on the charger base station 210, the Lithium-ion battery 277 in the charger is fully charged in approximately four hours. Once the battery 277 is fully charged, it has enough energy to fully recharge the implant battery 180 (FIG. 7A or FIG. 7B). If the charger 208 is not used and left on the charger base station 210, the battery 277 will self-discharge at a rate of about 10% per month.

Still with reference to FIG. 9, once the voltage of the battery 277 falls below a first prescribed limit, e.g., 4.1 VDC, during a standby mode, charging of the battery is automatically reinitiated. In addition, should the external charger battery 277 be discharged below a second prescribed limit, e.g., 2.5 VDC, the battery 277 is trickled charged until the voltage is above the second prescribed limit, at which point normal charging resumes.

A battery protection circuit 698 monitors if an over voltage, under voltage, or overcurrent condition occurs, and disconnects the battery, e.g, through opening at least one of the FET switches 701 and/or 702, or from the fault until normal operating conditions exist. Another switch 699, e.g., a thermal fuse, will disconnect the battery should the charging or discharging current exceed a prescribed maximum current for more than a prescribed time, e.g., 1.5 A for more than 10 seconds.

The battery 277 provides a power source for the RF amplifier 275. The RF amplifier, in a preferred embodiment, comprises a class E amplifier configured to drive a large alternating current through the coil 279.

Still with reference to FIG. 9, an alignment detection circuit 695 detects the presence of the IPG 100 through changes in the reflected impedance on the coil 279, as described above in connection with FIG. 7B. Reflected impedance is a minium when proper alignment has been obtained. This means that the steady-state voltage V1 sensed at the coil 279 is also at a minimum because maximum coupling occurs. When maximum coupling is detected, e.g., when V1 is at a minimum, an audible or visual alarm may sound. In a preferred embodiment, a first audible tone is generated whenever alignment is not achieved. Thus, as a charging operation begins, the first audible tone sounds, and the user seeks to position the charger 208 (or at least to position the coil 279) at a location that causes the first audible tone to cease. Similarly, a charge complete detection circuit 697 alerts the user through generation of a second audible tone (preferably an ON-OFF beeping sound) when the IPG battery 180 is fully charged. A fully charged condition is also sensed by monitoring the reflected impedance through the coil 279. As indicated above, a fully charged condition is signaled from the IPG by switching the rectifier circuit 682 within the IPG from a full-wave rectifier circuit to a half-wave rectifier circuit. When such rectifier switching occurs, the voltage V1 suddenly increases (e.g., a transient or pulsed component appears in the voltage V1) because the amount of reflected energy suddenly increases. This sudden increase in V1 is detected by the charge complete detection circuit 697, and once detected causes the second audible tone, or tone sequence, to be broadcast via the speaker 693 in order to signal the user that the implant battery 180 is fully charged.

Thus, it is seen that invention provides an implant device having a rechargeable internal battery as well as the control system used to monitor the battery's state of charge and circuitry to control the charging process. The system monitors the amount of energy used by the implant system and hence the state of charge of the battery. Through bidirectional telemetry (forward and back telemetry) with the hand held programmer 202 and/or the clinician programmer 204, the system is able to inform the patient or clinician of the status of the system, including the state of charge, and further make requests to initiate an external charge process when needed. The acceptance of energy from the external charger is entirely under the control of the implanted system. Advantageously, both physical and software control exist to ensure reliable and safe use of the recharging system.

Figure 10A:
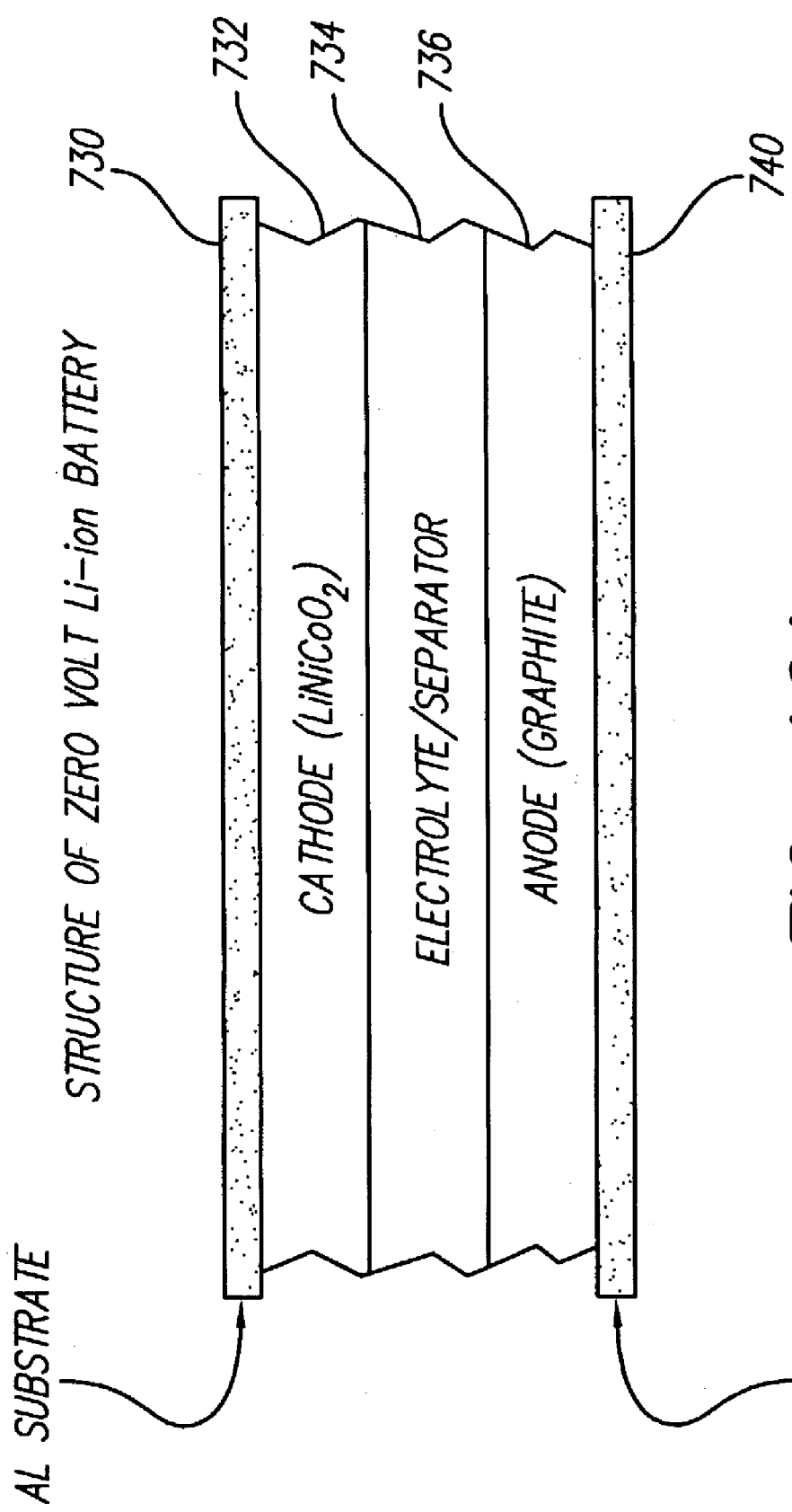
FIG. 10A depicts a sectional view of a preferred structure of a zero-volt technology lithium-ion battery usable with the invention.

As indicated previously, conventional lithium-ion batteries are not susceptible to being discharged to zero volts without suffering irreversible damage. In contrast, the present invention uses a lithium-ion or lithium-ion polymer battery that has been modified to allow a zero volt discharge condition to occur without causing irreversible damage to the battery. Such modified lithium-ion battery has a cell structure as depicted in FIG. 10A. As seen in FIG. 10A, the battery cell includes an anode 736 and a cathode 732. The anode is made from graphite that is placed on a titanium substrate 740. The cathode is preferably made from LiNiCoO$_2$ (lithium-nickel-cobalt oxide) that coats an aluminum (Al) substrate 730. An electrolyte and separator 734 separate the cathode from the anode.

The battery cell structure shown in FIG. 10A differs significantly from conventional Lithium-ion batteries. First, such a modified lithium-ion battery utilizes an anode (current-collector) electrode having a substrate that is made from titanium instead of copper. This allows the cell to drop to zero volts without causing irreversible damage. Second, the cathode electrode of the battery is made from LiNiCoO$_2$ instead of LiCoO2. Third, the separator used inside the battery is made from a ceramic instead of PE. Fourth, for a lithium-ion polymer battery, the electrolyte within the battery is preferably realized using a solid polymer conductor instead of LiPF6/EC+DEC, which is the electrolyte typically used in a lithium-ion battery. Additionally, the battery case may be coated with ferrite to further minimize eddy current heating. A "zero-volt technology" battery made in accordance with the present invention will always include at least the first modification mentioned above, i.e., an anode electrode having a substrate made from titanium (or a suitable titanium alloy), as opposed to copper, because this is the change needed to allow the battery cell voltage to drop to zero volts without causing irreversible damage to the battery cell.

Figure 10B:
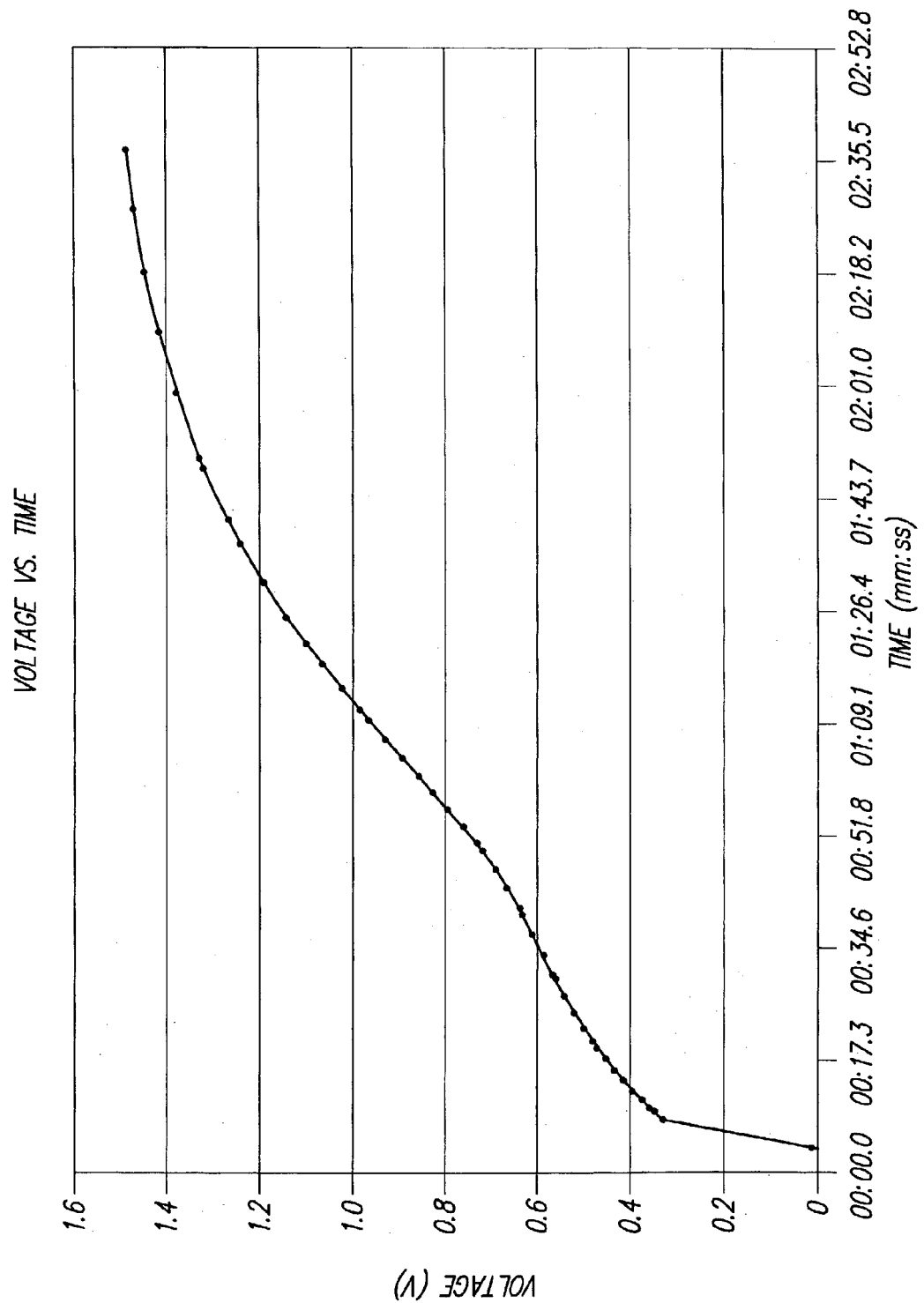
FIG. 10B depicts the battery voltage versus time when the lithium-Ion battery of FIG. 10A has been discharged to zero volts and is recharged using the recharging circuitry of the present invention.

When a modified lithium-ion battery as shown in FIG. 10A is discharged, it may discharge to zero volts without damage. When such a discharged-to-zero-volts battery is recharged, the voltage versus current relationship during the charging operation, assuming the charging circuit shown in FIG. 7A is employed, is substantially as shown in FIG. 10B. Of course, if the battery 180 has been discharged to zero volts, then no circuitry within the implant device may operate because there is no operating power. However, as soon as an external charger 208 begins coupling energy into the implant device, this energy is rectified and provides a dc operating voltage that allows the charge control IC 684 and battery protection IC 686 to begin to function, directing the appropriate charge current to the discharged battery 180. As seen in FIG. 10B, in a very short time, e.g., within about 10 seconds or so, the battery voltage will rise to about 0.3 V. From that initial starting point, the battery voltage gradually increases, almost in a linear manner, until it reaches about 1.5 volts after about being charged for about 2 minutes and 35 seconds. Thereafter, the battery continues to charge (not shown in FIG. 10B), until the battery voltage reaches a full charge of about 4.1 volts after about 2 hours or so.

Thus, as described above, it is seen that through use of a rechargeable internal battery 180 within the IPG 100, the SCS system and its control system are able to monitor the state of charge and control the charging process of the rechargeable battery 180. Through bi-directional telemetry (forward and back telemetry) with the hand held programmer 202 and/or the clinician programmer 204, the SCS system is able to inform the patient or clinician of the status of the system, including the state of charge, and further make requests to initiate an external charge process when needed. The acceptance of energy from the external charger is entirely under the control of the SCS implanted system. Advantageously, several layers of physical and software control exist to ensure reliable and safe use of the recharging system.

Also, as described above, it is seen that the invention provides a rechargeable system for use with a medical implant device or system that is characterized by the use or inclusion of: (1) lithium-ion or lithium-ion polymer batteries; (2) lithium-ion zero volt battery technology; (3) misalignment indication at the external location, responsive to changes in reflected impedance from the implant location; (4) a rechargeable recharger; (5) adhesive and/or Velcro®/ adhesive charger attachment means; (6) over and under charge protection circuitry, including automatic shut-off circuitry; (7) back telemetry of implant battery charge level to external hand-held or clinician's programmer; (8) an end of charging modulating indicator within the implant device; (9) a battery status indicator on the external charger device; and (10) single or dual rate charging circuitry, i.e., fast charging at the safer lower battery voltages, and slower charging when the battery is nearer to full charge higher battery voltages.

While the invention herein disclosed has been described by means of specific embodiments and applications thereof, numerous modifications and variations could be made thereto by those skilled in the art without departing from the scope of the invention set forth in the claims.

What is claimed is:

1. An implantable pulse generator (IPG) system for use with a spinal cord stimulation system, the IPG system comprising an implantable pulse generator and an external portable charger, wherein the IPG comprises:

an hermetically sealed case;

electronically circuitry including memory circuits, housed within said hermetically sealed case, said electronic circuitry including a multiplicity of independent bi-directional output current sources, each output current source being connected to an electrode node;

a multiplicity of coupling capacitors, each coupling capacitor being connected to a respective one of said electrode nodes;

a header connecter attached to said sealed case, the header connecter having a multiplicity of feedthrough pins that pass therethrough, wherein each of said multiplicity of coupling capacitors is connected on the sealed side of said case to one of said feedthrough pins;

an electrode array having a multiplicity of electrodes thereon external to said sealed case, wherein each electrode of the multiplicity of electrodes is detachably electrically connected to one of said feedthrough pins on a nonsealed side of said sealed case;

wherein each output current source generates an output stimulus current having a selected amplitude and polarity that, when the output current source is enabled, is directed to the electrode connected thereto through its respective feedthrough pin and coupling capacitor;

a rechargeable lithium-ion battery adapted to operate over a wide range of voltages ranging from zero volts to a fully-charged voltage, said rechargeable battery having an anode electrode having a substrate made from titanium, said rechargeable battery providing operating power for the electronic circuitry;

a secondary coil;

a rectifier circuit; and battery charger and protection circuitry that receives externally generated energy through the secondary coil and rectifier circuit, and uses the externally generated energy to charge the rechargeable lithium-ion battery.

2. The IPG system of claim 1 wherein the portable charger comprises:

a second rechargeable battery;

a recharging base station that recharges the second rechargeable battery from energy obtained from line ac power;

a primary coil;

a power amplifier for applying ac power derived from the second rechargeable battery to the primary coil;

a back telemetry receiver for monitoring the magnitude of the ac power at the primary coil as applied by the power amplifier, thereby monitoring reflected impedance associated with energy magnetically coupled through the primary coil; and an alarm generator that generates an audible alarm signal in response to changes sensed in the reflected impedance monitored by the back telemetry receiver.

3. The IPG system of claim 2 wherein the back telemetry receiver comprises:

alignment detection circuitry that detects when the primary coil is properly aligned with the secondary coil included within the IPG for maximum power transfer; and charge complete detection circuitry that detects when the battery within the IPG is fully charged.

4. The IPG system of claim 3 wherein the alignment detection circuitry causes the alarm generator to broadcast a first audible tone when the primary coil is misaligned with the secondary coil, whereby the first audible tone stops being broadcast when the primary coil is properly aligned with the secondary coil.

5. The IPG system of claim 4 wherein the battery charger and protection circuitry within the IPG comprises:

monitoring circuitry that monitors the voltage of the rechargeable battery and the charging current flowing to the rechargeable battery; and wherein the rectifier circuit is switchable between a full-wave rectifier circuit and a half-wave rectifier circuit, and wherein the rectifier circuit is switched to operate as a full-wave rectifier circuit during charging of the rechargeable battery, and wherein the rectifier circuit switches to a half-wave rectifier circuit when the rechargeable battery voltage and rechargeable battery charging current reach prescribed levels, which prescribed levels indicate the rechargeable battery is fully charged, whereby modulation of the rectifier circuit between a full-wave rectifier circuit and a half-wave rectifier circuit is used to indicate whether the rechargeable battery is fully charged; and wherein a change in reflected impedance at the primary coil indicates a switching of the rectifier circuit from a full-wave rectifier circuit to a half-wave rectifier circuit, and hence indicates whether the rechargeable battery is fully charged.

* * * * *